US007183436B2

(12) United States Patent
Sundermann et al.

(10) Patent No.: US 7,183,436 B2
(45) Date of Patent: Feb. 27, 2007

(54) SUBSTITUTED 4-AMINOCYCLOHEXANOLS

(75) Inventors: Bernd Sundermann, Aachen (DE); Hagen-Heinrich Hennies, Simmerath (DE); Werner Englberger, Stolberg (DE); Stephan Wnendt, Aachen (DE)

(73) Assignee: Gruenenthal GmbH, Aachen (DE)

( * ) Notice: Subject to any disclaimer, the term of this patent is extended or adjusted under 35 U.S.C. 154(b) by 186 days.

(21) Appl. No.: 10/758,242

(22) Filed: Jan. 16, 2004

(65) Prior Publication Data

US 2004/0236104 A1 Nov. 25, 2004

Related U.S. Application Data

(63) Continuation of application No. PCT/EP02/07842, filed on Jul. 15, 2002.

(30) Foreign Application Priority Data

Jul. 17, 2001 (DE) .............................. 101 35 636

(51) Int. Cl.
*C07C 211/38* (2006.01)
*C07D 277/62* (2006.01)
*C07D 209/04* (2006.01)
*C07D 333/56* (2006.01)
*C07D 333/72* (2006.01)
*C07D 317/72* (2006.01)
*C07D 307/94* (2006.01)

(52) U.S. Cl. ................ 564/307; 548/179; 548/469; 549/58; 549/341; 549/469; 514/367; 514/415; 514/443; 514/462; 514/469; 514/647

(58) Field of Classification Search ............... None
See application file for complete search history.

(56) References Cited

U.S. PATENT DOCUMENTS

| 4,115,589 A | 9/1978 | Lednicer |
| 4,212,878 A | 7/1980 | Lednicer et al. |
| 4,346,101 A | 8/1982 | Lednicer |
| 4,366,172 A | 12/1982 | Lednicer |
| 5,239,110 A | 8/1993 | Mallamo et al. |
| 5,304,479 A | 4/1994 | Lin |

FOREIGN PATENT DOCUMENTS

| DE | 2839891 | 4/1979 |
| DE | 19963175 | 7/2001 |
| EP | 0410191 | 1/1991 |
| WO | WO 01/12195 | 2/2001 |

OTHER PUBLICATIONS

Database CAPLUS on STN, Acc. No. 1987:423027, Swahn et al., Report (1985), FOA-C-40220-C1; Order No. PB86-129921/GAR, 21 pp. Avail.:NTIS From: Gov. Rep. Announce. Index (US) 1986, 86(7), Abstract No. 613-507 (abstract).*

Daniel Lednicer et al., "4-(p-Bromophenyl)-4-(dimethylamino)-1-phenethylcyclohexanol, an Extremely Potent Representative of a New Analgesic Series", Journal of Medicinal Chemistry, Oct. 1979, pp. 1157-1158, vol. 22, No. 10, American Chemical Society.

Hiroshi Kawamoto et al., "Synthesis of J-113397, the First Potent and Selective ORL1 Antagonist," Tetrahedron, 2001, pp. 981-986, 57, Elsevier Science Ltd.

Faud A. Abdulla et al., "Axotomy Reduces the Effect of Analgesic Opioids Yet Increases the Effect of Nociceptin on Dorsal Root Ganglion Neurons," The Journal of Neuroscience, Dec. 1, 1998, pp. 9685-9694, 18, 23, Society for Neuroscience.

Girolamo Calo et al., "Pharmacology of Nociceptin and its Receptor: A Novel Therapeutic Target," British Journal of Pharmacology, 2000, pp. 1261-1283, 129, Macmillan Publishers Ltd.

Mark Conner et al., "The Effect of Nociceptin on $Ca^{2+}$ Channel Current and Intracellular $Ca^{2+}$ in the SH-SY5Y Human Neuroblastoma Cell Line", 1996, pp. 205-207, 118, Stockton Press.

E.S.L. Faber et al., "Depression of Glutamatergic Transmission by Nociceptin in the Neonatal Rat Hemisected Spinal Cord Preparation In Vitro", Special Report, Jul. 19, 1996, pp. 1-2.

"Opioid and Opiate Receptors: Peptides and Knock-Out," Society for Neuroscience, 1998, p. 1358, vol. 24.

Francois Jenck et al., "Orphanin FQ Acts as an Anxiolytic to Attenuate Behavioral Responses to Stress," Proc. Natl. Acad. Sci., Dec. 1997, pp. 14854-14858, vol. 94, USA.

Michael A. King et al., "Spinal Analgesic Activity of Orphanin FQ/Nociceptin and its Fragments", Neuroscience Letters, 1997, pp. 113-116, 223, Elsevier Science Ireland Ltd.

Toshiya Manabe et al., "Facilitation of Long-Term Potentiation and Memory in Mice Lacking Nociceptin Receptors", Letters To Nature, Aug. 6, 1998, pp. 577-581, vol. 394, Macmillan Publishers Ltd.

Jean-Claude Meunier et al., "Isolation and Structure of the Endogenous Agonist of Opiod Receptor-Like $ORL_1$ Receptor," Letters to Nature, Oct. 12, 1995, pp. 532-535, vol. 377.

J.S. Mogil et al., "Orphanin FQ is a Functional Anti-Opioid Peptide", Neuroscience, 1996, pp. 333-337, vol. 75, No. 2, Elsevier Science Ltd., Great Britain.

Miyuki Nishi et al., "Unrestrained Nociceptive Response and Disregulation of Hearing Ability in Mice Lacking the Nociceptin/OrphaninFQ Receptor," The EMBO Journal, 1997, pp. 1858-1864, vol. 16, No. 8, Oxford University Press.

Rainer K. Reinscheid et al., "Orphanin FQ: A Neuropeptide That Activates an Opioldlike G Protein-Coupled Receptor," Science, Nov. 3, 1995, pp. 792-794, vol. 270.

(Continued)

*Primary Examiner*—Brian Davis
(74) *Attorney, Agent, or Firm*—Crowell & Moring LLP

(57) ABSTRACT

Substituted 4-aminocyclohexanols, methods of producing the same, pharmaceuticals containing these compounds, the use of substituted 4-aminocyclohexanols for producing pharmaceutical compositions for the treatment of various indications, in particular pain, and for related treatment methods.

52 Claims, No Drawings

OTHER PUBLICATIONS

Christopher W. Vaughan et al., "Increase by the $ORL_1$ Receptor (Opioid Receptor-like$_1$) Ligand, Nociceptin, of Inwardly Rectifying K Conductance in Dorsal Raphe Nucleus Neurones," Special Report, pp. 1609-1611.

Tatsuo Yamamoto et al., "Effects of Intrathecally Administered Nociceptin, an Opioid Receptor-like$_1$ Receptor Agonist, and N-methyl-D-aspartate Receptor Antagonist on the Thermal Hyperalgesia Induced by Partial Sciatic Nerve Injury in the Rat," Anesthesiology, 1997, pp. 1145-1152, vol. 87, No. 5, Lippincott-Raven Publishers.

Ali Ardati et al., "Interaction of [$^3$H]Orphanin FQ and $^{125}$I-Tyr14-Orphanin FQ with the Orphanin FQ Receptor: Kinetics and Modulation by Cations and Guanine Nucleotides," Molecular Pharmacology, 1997, pp. 816-824, 51, The American Society for Pharmacology and Experimental Therapeutics.

Hunter C. Champion et al., "[Tyr$^1$]-Nociceptin, a Novel Nociceptin Analog, Decreases Systemic Arterial Pressure by a Naloxone-Insensitive Mechanism in the Rat," Biochemical and Biophysical Research Communications, 1997, pp. 309-312, 234, Academic Press.

Tristan Darland et al., "Orphanin FQ/nociceptin: a Role in Pain and Analgesia, But So Much More," TINS, 1998, pp. 215-221, vol. 21, No. 5, Elsevier Science Ltd.

Bulent Gumusel et al., "Nociceptin: An Endogenous Agonist for Central Opioid Like$_1$ ($ORL_1$) Receptors Possesses Systemic Vasorelaxant Properties," Life Sciences, 1997, pp. PL 141-145, vol. 60, No. 8, Elsevier Science Inc., USA.

Naoki Hara et al., "Characterization of Nociceptin Hyperalgesia and Allodynia in Conscious Mice," British Journal of Pharmacology, 1997, pp. 401-408, 121, Stockton Press.

Daniel R. Kapusta et al., "Diuretic and Antinatriuretic Responses Produced by the Endogenous Opioid-Like Peptide, Nociceptin (Orphanin FQ)," Life Sciences, 1997, pp. PL 15-21, vol. 60, No. 1, Elsevier Science Inc., USA.

Frederic Knoflach et al., "Modulation of Voltage-Gated Calcium Channels by Orphanin FQ in Freshly Hippocampal Neurons," The Journal of Neuroscience, Nov. 1, 1996, pp. 6657-6664, 16, 21, Society for Neuroscience.

Hans Matthes et al., "Functional Selectivity of Orphanin FQ for Its Receptor Coexpressed with Potassium Channel Subunits in Xenopus *laevis* Oocytes," Molecular Pharmacology, 1996, pp. 447-450, 50, The American Society for Pharmacology and Experimental Therapeutics.

Jeffrey S. Mogil et al., "Functional Antagonism of μ-, Σ- and Θ-opioid Antinociception by Orphanin FQ," Neuroscience Letters, 1996, pp. 131-134, 214, Elsevier Science Ireland Ltd.

Catherine Mollereau et al., "ORL1, A Novel Members of the Opioids Receptor Family Cloning, Functional Expression and Localization," FEBS Letters, 1994, 341, Federation of European Biochemical Societies.

James D. Pomonis et al., "Orphanin FQ, Agonist of Orphan Opioid Receptor $ORL_1$, Stimulates Feeding in Rats," NeuroReport, Dec. 20, 1996, pp. 369-371, vol. 8, No. 1, Rapid Science Publishers.

Y.-S. Shu et al., "Orphanin FQ/Nociceptin Modulates Glutamate- and Kainic Acid-Induced Currents in Acutely Isolated Rat Spinal Dorsal Horn Neurons," Neuropeptides, 1998, pp. 567-571, 32, Harcourt Brace & Co., Ltd.

Xiao-Jun Xu et al., "Nociceptin or Antinociceptin: Potent Spinal Antinociceptive Effect of Orphanin FQ/ Nociceptin in the Rat," NeuroReport, Sep. 2, 1996, vol. 17, No. 13, Rapid Science Publishers.

T. Yamamoto et al., "Analgesic Effect of Intrathecally Administered Nociceptin, an Opioid Receptor-Like$_1$ Receptor Agonist, in the Rat Formalin Test," Neuroscience, 1997, pp. 249-254, vol. 81, Elsevier Science Ltd.

M.N.A. Rao et al., "Quantitative Correlation Between Hydrophobicity and Analgesis Activity of 4-Amino 4-Arylcyclohexanols," Indian Drugs, 1985, pp. 252-257, 22, 5.

Jean-Marc Kamenka et al., "Orientation Structurale et Conformationnelle de la Fixation de la Phencyclidine dans le SNC," Eur. J. Med. Chem. 1984, pp. 255-260, 19, 3.

Daniel Lednicer et al., "4-Amino-4-arylclohexanones and Their Derivatives, a Novel Class of Analgestics", J. Med. Chem., 1980, pp. 424-430, 23.

Von Voigtlander et al., "4-Aryl-4-Aminocyclohexanone Derivatives: A Chemically Novel Series of Analgesics Including Opioid Antagonists and Extremely Potent Agonists," *Endog. Exog. Opiate Agonists Antagonists*, Proc. Int. Narc. Res. Club. Conf., 1980 (Meeting Date 1979), pp. 17-21, Pergamon, Elmsford, NY, USA.

* cited by examiner

SUBSTITUTED 4-AMINOCYCLOHEXANOLS

CROSS-REFERENCE TO RELATED APPLICATIONS

This application is a continuation of International Patent Application No. PCT/EP02/07842, filed Jul. 15, 2002, designating the United States of America, and published in German as WO 03/008370 A1, the entire disclosure of which is incorporated herein by reference. Priority is claimed based on Federal Republic of Germany Patent Application No. DE 101 35 636.6, filed Jul. 15, 2001.

FIELD OF THE INVENTION

The present invention relates to substituted 4-aminocyclohexanols, to methods of producing them, to pharmaceuticals containing these compounds, to the use of substituted 4-aminocyclohexanols for producing pharmaceutical compositions for the treatment of various indications, in particular pain, and for related treatment methods.

BACKGROUND OF THE INVENTION

The heptadecapeptide nociceptin is an endogenous ligand of the ORL1 (Opioid-Receptor-Like) receptor (Meunier et al., Nature 377, 1995, pp. 532–535), which belongs to the family of opioid receptors and may be found in many regions of the brain and the spinal cord (Mollereau et al., FEBS Letters, 341, 1994, pp. 33–38, Darland et al., Trends in Neurosciences, 21, 1998, pp. 215–221). The peptide is characterized by a high affinity, with a $K_d$ value of approximately 56 pM (Ardati et al., Mol. Pharmacol. 51, pp. 816–824), and by high selectivity for the ORL1 receptor. The ORL1 receptor is homologous to the μ, κ and δ opioid receptors and the amino acid sequence of the nociceptin peptide has a marked similarity to those of the known opioid peptides. The activation of the receptor induced by the nociceptin leads, via the coupling with $G_{i/o}$ proteins to inhibition of the adenylate cyclase (Meunier et al., Nature 377, 1995, pp. 532–535). On the cellular plane also, there are functional similarities between the μ, κ and δ opioid receptors and the ORL1 receptor with respect to activation of the potassium channel (Matthes et al., Mol. Pharmacol. 50, 1996, pp. 447–450; Vaughan et al., Br. J. Pharmacol. 117, 1996, pp. 1609–1611) and inhibition of the L-, N- and P/Q-type calcium channels (Conner et al., Br. J. Pharmacol. 118, 1996, pp. 205–207; Knoflach et al., J. Neuroscience 16, 1996, pp. 6657–6664).

After intercerebroventicular application, the nociceptin peptide exhibits pronociceptive and hyperalgesic activity in various animal models (Reinscheid et al., Science 270, 1995, pp. 792–794; Hara et al., Br. J. Pharmacol. 121, 1997, pp. 401–408). These findings may be explained as inhibition of stress-induced analgesia (Mogil et al., Neurosci. Letters 214, 1996, pp. 131–134; and also Neuroscience 75, 1996, pp. 333–337). In this connection, anxiolytic activity of the nociceptin could also be demonstrated (Jenck et al., Proc. Natl. Acad. Sci. USA 94, 1997, 14854–14858).

On the other hand, an antinociceptive effect of nociceptin could be demonstrated in various animal models, in particular after intrathecal administration. Nociceptin inhibits the activity of kainate- or glutamate-stimulated dorsal root ganglion neurons (Shu et al., Neuropeptides, 32, 1998, 567–571) or glutamate-stimulated spinal cord neurons (Faber et al., Br. J. Pharmacol., 119, 1996, pp. 189–190); it has an antinociceptive effect in the tail flick test in mice (King et al., Neurosci. Lett., 223, 1997, 113–116), in the flexor-reflex model in rats (Xu et al., NeuroReport, 7, 1996, 2092–2094) and in the formalin test on rats (Yamamoto et al., Neuroscience, 81, 1997, pp. 249–254). In models of neuropathic pain, an antinociceptive effect of nociceptin, which is of interest in so far as the effectiveness of nociceptin increases after axotomy of spinal nerves, could be demonstrated (Yamamoto and Nozaki-Taguchi, Anesthesiology, 87, 1997). This is in contrast to conventional opioids, of which the effectiveness decreases under these conditions (Abdulla and Smith, J. Neurosci., 18, 1998, pp. 9685–9694).

The ORL1 receptor also participates in the regulation of further physiological and pathophysiological processes. These include learning and memory formation (Sandin et al., Eur. J. Neurosci., 9, 1997, pp. 194–197; Manabe et al., Nature, 394, 1997, pp. 577–581), hearing ability (Nishi et al., EMBO J., 16, 1997, pp. 1858–1864), assimilation of food (Pomonis et al., NeuroReport, 8, 1996, pp. 369–371), regulation of blood pressure (Gumusel et al., Life Sci., 60, 1997, pp. 141–145; Campion and Kadowitz, Biochem. Biophys. Rep. Comm., 234, 1997, pp. 309–312), epilepsy (Gutierrez et al. Abstract 536.18, Society for Neuroscience, Vol. 24, 28th Ann. Meeting, Los Angeles, 7–12 Nov. 1998) and diuresis (Kapisa et al., Life Sciences, 60, 1997, PL 15–21). In an article by Calo et al. (Br. J. Pharmacol., 129, 2000, 1261–1283) an overview is given of the indications or biological processes in which the ORL1 receptor plays a part or could very probably play a part. These include: analgesia, stimulation and regulation of food assimilation, influence on μ agonist such as morphine, treatment of withdrawal symptoms, reduction of addiction potential of morphines, anxiolysis, modulation of movement activity, memory defects, epilepsy; modulation of neurotransmitter discharge, in particular of glutamate, serotonin and dopamine, and therefore neurodegenerative diseases; influencing of the cardiovascular system, triggering of an erection, diuresis, antinatriuresis, electrolyte management, arterial blood pressure, water retention diseases, intestinal motility (diarrhea), relaxing effects on the respiratory tracts, micturation reflex (urinary incontinence). The use of agonist and antagonist as anoretics, analgesics (also in co-administration with opioids) or nootropics, but also as antitussives is also discussed.

The possible applications of compounds which bind to the ORL1 receptor and activate or inhibit it are correspondingly varied.

SUMMARY OF THE INVENTION

One object of the present invention is to provide active ingredients which act on the nonceiceptin/ORL1 receptor system and are therefore suitable for pharmaceutical compositions, in particular for treating the various diseases associated with this system according to the prior art or for use in the indications mentioned therein.

The invention accordingly relates to substituted 4-aminocyclohexanols described hereinafter as substance group A corresponding to formula I,

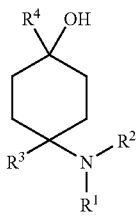

wherein
- $R^1$ and $R^2$ independently of one another are selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl; wherein $R^1$ and $R^2$ are not both H,
- or the radicals $R^1$ and $R^2$ together form a ring and represent $CH_2CH_2OCH_2CH_2$, $CH_2CH_2NR^5CH_2CH_2$ or $(CH_2)_{3-6}$,
  - where $R^5$ is selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl;
- $R^3$ is selected from respectively unsubstituted or singly or multiply substituted aryl or heteroaryl;
- $R^4$ is selected from respectively unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$
  - where Y=O, S or $H_2$,
  - where $R^6$ is selected from
    - H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
  - where $R^7$ is selected from
    - H; respectively unsubstituted or singly or multiply substituted $C_{3-8}$-cycloalkyl, aryl or heteroaryl,
  - where $R^8$ is selected from
    - respectively unsubstituted or singly or multiply substituted aryl or heteroaryl,
    - where L is selected from
      - —$C(O)$—$NH$—, —$NH$—$C(O)$—, —$C(O)$—$O$—, —$O$—$C(O)$—, —$O$—, —$S$— or —$S(O)_2$—
  - where $R^9$ is selected from
    - respectively unsubstituted or singly or multiply substituted aryl or heteroaryl,
  - provided that,
    - (disclaimer group 1) if $R^3$=substituted or unsubstituted phenyl, and $R^4$=substituted or unsubstituted phenyl or —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$
      - where Y=$H_2$
      - $R^6$=H, saturated or unsaturated, branched or unbranched, singly or multiply substituted or unsubstituted $C_{1-5}$-alkyl, and/or
      - $R^7$=H, respectively substituted or unsubstituted $C_{3-8}$-cycloalkyl or phenyl,
      - $R^1$ and $R^2$ independently of one another are not both $C_{1-5}$-alkyl,
        - (disclaimer group 2) if $R^3$=substituted or unsubstituted thiophenyl, and $R^4$=—$CH_2$—$CH_2$-phenyl the radicals $R^1$ and $R^2$ do not together form a ring and represent $(CH_2)_5$, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

All these compounds or groups of compounds according to the invention display excellent binding to the ORL1 receptor.

Compounds which display a certain remote structural relationship with the compounds proposed here are known from the following documents:

- DE-OS-28 39 891 or the parallel U.S. Pat. No. 4,366,172 (Lednicer et al.). The aforementioned compounds are described therein as analgesically active, with reference to the ORL1 receptor.
- the parallel articles:
  - D. Lednicer and P. F. of Voightlunder, J. Med. Chem. 1979, 22, 1157,
  - D. Lednicer, P. F. of Voightlunder and D. E. Emmert, J. Med. Chem. 1980, 23, 424, and
  - D. Lednicer, P. F. of Voightlunder and D. E. Emmert, J. Med. Chem. 1981, 24, 404,
  - D. Lednicer, P. F. of Voightlunder and D. E. Emmert, J. Med. Chem. 1981, 24, 340,
  - P. F. Von Voightlunder, D. Lednicer, R. A. Lewis and D. D. Gay, "Endogenous and Exogenous Opiate Agonist and Antagonist", Proc. Int. Narc. Rep. Club Conf. (1980), Meeting Date 1979, Way E. Long (Ed), Publisher: Pergamon, Elmsford, N.Y. International, Pergamon, 1980, 17–21,
  - Kamenka et al., Eur. J. Med. Chem. Chim. Ther.; FR; 19; 3; 1984; 255–260 and
  - Rao M. N. A. and Rao pp. C. Indian Drugs, 1985, 22 (5), 252–257.

U.S. Pat. No. 5,304,479 belonging to Lin et al. is also related to the claimed compounds. Compounds (disclaimer group 3) in which $R^3$ is unsubstituted phenyl, $R^4$ is selected from —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH^2$—$CH_2$—$CH_2R^7$ where Y=$H_2$, $R^6$=H, saturated or unsaturated, branched or unbranched, singly or multiply substituted or unsubstituted $C_{1-7}$-alkyl, and $R^7$=H and the radicals $R^1$ and $R^2$ together form a ring and represent $(OH_2)_5$ are therefore optionally also excluded from substance protection. Under certain circumstances, compounds (disclaimer group 4), in which $R^3$ is unsubstituted phenyl, the radicals $R^1$ and $R^2$ together form a ring and represent $(CH_2)_5$ and $R^4$ is selected from —$CHR^6R^7$, —$CHR^6$—$CH_2R^7$, —$CHR^6$—

CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$^2$—CH$_2$—CH$_2$R$^7$ where Y=O or S, R$^6$=H, saturated or unsaturated, branched or unbranched, singly or multiply substituted or unsubstituted C$_{1-7}$-alkyl, or saturated or unsaturated, branched or unbranched, singly or multiply substituted or unsubstituted C(O)O—C$_{1-6}$-alkyl; and R$^7$=H may also be excluded from substance protection.

Under certain circumstances it may be preferred if the compounds in disclaimer group 1 (see above) excluded from protection are worded more broadly and the disclaimer accordingly reads:

provided that,
(disclaimer group 1a) if R$^3$=substituted or unsubstituted aryl, and R$^4$=substituted or unsubstituted phenyl or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—H$_2$R$^7$
where Y=H$_2$
R$^6$=H, saturated or unsaturated, branched or unbranched, singly or multiply substituted or unsubstituted C$_{1-5}$-alkyl, and/or
R$^7$=H, respectively substituted or unsubstituted C$_{3-8}$-cycloalkyl or phenyl,
R$^1$ and R$^2$ independently of one another are not both C$_{1-5}$-alkyl, provided that,
(disclaimer group 1b) if R$^3$=substituted or unsubstituted phenyl, and R$^4$=respectively substituted or unsubstituted C$_{3-8}$-cycloalkyl or aryl; or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$
where Y=H$_2$
R$^6$=H, saturated or unsaturated, branched or unbranched, singly or multiply substituted or unsubstituted C$_{1-5}$-alkyl, and/or
R$^7$=H, respectively substituted or unsubstituted C$_{3-8}$-cycloalkyl or phenyl,
R$^1$ and R$^2$ independently of one another are not both C$_{1-5}$-alkyl, provided that,
(disclaimer group 1c) if R$^3$=substituted or unsubstituted phenyl, and R$^4$=respectively substituted or unsubstituted heteroaryl, C$_{3-8}$-cycloalkyl or aryl; or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$
where Y=H$_2$
R$^6$=H, saturated or unsaturated, branched or unbranched, singly or multiply substituted or unsubstituted C$_{1-5}$-alkyl, and/or
R$^7$=H, respectively substituted or unsubstituted C$_{3-8}$-cycloalkyl or phenyl,
R$^1$ and R$^2$ independently of one another are not both C$_{1-5}$-alkyl, provided that,
(disclaimer group 1d) if R$^3$=substituted or unsubstituted aryl, and R$^4$=substituted or unsubstituted aryl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$
where Y=H$_2$
R$^6$=H, saturated or unsaturated, branched or unbranched, singly or multiply substituted or unsubstituted C$_{1-5}$-alkyl, and/or
R$^7$=H, respectively substituted or unsubstituted C$_{3-8}$-cycloalkyl or phenyl,
R$^1$ and R$^2$ independently of one another are not both C$_{1-5}$-alkyl, provided that,
(disclaimer group 1e) if R$^3$=substituted or unsubstituted phenyl, and R$^4$=substituted or unsubstituted phenyl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$
where Y=H$_2$
R$^6$=H, saturated or unsaturated, branched or unbranched, singly or multiply substituted or unsubstituted C$_{1-7}$-alkyl, and/or
R$^7$=H, respectively substituted or unsubstituted C$_{3-8}$-cycloalkyl or aryl,
R$^1$ and R$^2$ independently of one another are not both C$_{1-8}$-alkyl, provided that,
(disclaimer group 1f) if R$^3$=substituted or unsubstituted phenyl, and R$^4$=substituted or unsubstituted phenyl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$
where Y=H$_2$
R$^6$=H, saturated or unsaturated, branched or unbranched, singly or multiply substituted or unsubstituted C$_{1-7}$-alkyl, and/or
R$^7$=H, respectively substituted or unsubstituted C$_{3-8}$-cycloalkyl, heteroaryl or aryl,
R$^1$ and R$^2$ independently of one another are not both C$_{1-5}$-alkyl, provided that,
(disclaimer group 1g) if R$^3$=substituted or unsubstituted aryl, and R$^4$=substituted or unsubstituted aryl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$
where Y=H$_2$
R$^6$=H, saturated or unsaturated, branched or unbranched, singly or multiply substituted or unsubstituted C$_{1-7}$-alkyl, and/or R$^7$=H, respectively substituted or unsubstituted C$_{3-8}$-cycloalkyl or aryl,
R$^1$ and R$^2$ independently of one another are not both C$_{1-8}$-alkyl, provided that,
(disclaimer group 1h) if R$^3$=substituted or unsubstituted aryl, and R$^4$=substituted or unsubstituted aryl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$
where Y=H$_2$
R$^6$=H, saturated or unsaturated, branched or unbranched, singly or multiply substituted or unsubstituted C$_{1-7}$-alkyl, and/or $R^7$=H, respectively substituted or unsubstituted $C_{3-8}$-cycloalkyl, heteroaryl or aryl $R^1$ and $R^2$ independently of one another are not both $C_{1-8}$-alkyl, provided that,
(disclaimer group 1j) if $R^3$=substituted or unsubstituted aryl, and $R^4$=respectively substituted or unsubstituted aryl or $C_{3-8}$-cycloalkyl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ where Y=H$_2$ $R^6$=H, saturated or unsaturated, branched or unbranched, singly or multiply substituted or unsubstituted $C_{1-7}$-alkyl, and/or $R^7$=H, respectively substituted or unsubstituted $C_{3-8}$-cycloalkyl or aryl $R^1$ and $R^2$ independently of one another are not both $C_{1-8}$-alkyl, provided that,
(disclaimer group 1k) if $R^3$=substituted or unsubstituted aryl, and $R^4$=respectively substituted or unsubstituted aryl, heteroaryl or $C_{3-8}$-cycloalkyl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ where Y=H$_2$ $R^6$=H, saturated or unsaturated, branched or unbranched, singly or multiply substituted or unsubstituted $C_{1-7}$-alkyl, and/or $R^7$=H, respectively substituted or unsubstituted $C_{3-8}$-cycloalkyl or aryl $R^1$ and $R^2$ independently of one another are not both $C_{1-8}$-alkyl, provided that,
(disclaimer group 1l) if $R^3$=substituted or unsubstituted aryl, and $R^4$=respectively substituted or unsubstituted aryl, heteroaryl or $C_{3-8}$-cycloalkyl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ where Y=H$_2$ $R^6$=H, saturated or unsaturated, branched or unbranched, singly or multiply substituted or unsubstituted $C_{1-7}$-alkyl, and/or $R^7$=H, respectively substituted or unsubstituted $C_{3-8}$-cycloalkyl, heteroaryl or aryl $R^1$ and $R^2$ independently of one another are not both $C_{1-8}$-alkyl, provided that,
(disclaimer group 1m) if $R^3$=substituted or unsubstituted aryl or heteroaryl, and $R^4$=respectively substituted or unsubstituted aryl or $C_{3-8}$-cycloalkyl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ where Y=H$_2$ $R^6$=H, saturated or unsaturated, branched or unbranched, singly or multiply substituted or unsubstituted $C_{1-7}$-alkyl, and/or $R^7$=H, respectively substituted or unsubstituted $C_{3-8}$-cycloalkyl or aryl $R^1$ and $R^2$ independently of one another are not both $C_{1-8}$-alkyl, provided that,
(disclaimer group 1n) if $R^3$=substituted or unsubstituted aryl or heteroaryl, and $R^4$=substituted or unsubstituted aryl or $C_{3-8}$-cycloalkyl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ where Y=H$_2$ $R^6$=H, saturated or unsaturated, branched or unbranched, singly or multiply substituted or unsubstituted $C_{1-7}$-alkyl, and/or $R^7$=H, respectively substituted or unsubstituted $C_{3-8}$-cycloalkyl, heteroaryl or aryl $R^1$ and $R^2$ independently of one another are not both $C_{1-8}$-alkyl, provided that
(disclaimer group 1o) if $R^3$=substituted or unsubstituted aryl or heteroaryl, and $R^4$=respectively substituted or unsubstituted aryl, heteroaryl or $C_{3-8}$-cycloalkyl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ where Y=H$_2$ $R^6$=H, saturated or unsaturated, branched or unbranched, singly or multiply substituted or unsubstituted $C_{1-7}$-alkyl, and/or $R^7$=H, respectively substituted or unsubstituted $C_{3-8}$-cycloalkyl or aryl $R^1$ and $R^2$ independently of one another are not both $C_{1-8}$-alkyl, or provided that,
(disclaimer group 1p) if $R^3$=substituted or unsubstituted aryl or heteroaryl, and $R^4$=respectively substituted or unsubstituted aryl, heteroaryl or $C_{3-8}$-cycloalkyl, or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ where Y=H$_2$ $R^6$=H, saturated or unsaturated, branched or unbranched, singly or multiply substituted or unsubstituted $C_{1-7}$-alkyl, and/or $R^7$=H, respectively substituted or unsubstituted $C_{3-8}$-cycloalkyl, heteroaryl or aryl $R^1$ and $R^2$ independently of one another are not both $C_{1-8}$-alkyl.

Under certain circumstances it may be preferred if the compounds excluded from protection in disclaimer group 2 (see above) are worded somewhat more broadly and the disclaimer accordingly reads:

provided that
(disclaimer group 2a) if $R^3$=substituted or unsubstituted heteroaryl, and $R^4$=—CH$_2$—CH$_2$-phenyl,
the radicals $R^1$ and $R^2$ do not together form a ring and represent (CH$_2$)$_5$, provided that
(disclaimer group 2b) if $R^3$=substituted or unsubstituted thiophenyl, and $R^4$=—CH$_2$—CH$_2$-aryl,
the radicals $R^1$ and $R^2$ do not together form a ring and represent (CH$_2$)$_5$, provided that
(disclaimer group 2c) if $R^3$=substituted or unsubstituted thiophenyl, and $R^4$=—$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH^2$—$CH_2R^7$ or —$C(Y)$—$CH_2$—$CH_2$—$CH_2R^7$
where $Y=H_2$
$R^6$=H and
$R^7$=substituted or unsubstituted phenyl the radicals $R^1$ and $R^2$ do not together form a ring and represent $(CH_2)_5$, provided that
(disclaimer group 2d) if $R^3$=substituted or unsubstituted thiophenyl, and $R^4$=—$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH^2$—$CH_2R^7$ or —$C(Y)$—$CH_2$—$CH_2$—$CH_2R^7$,
where $Y=H_2$
$R^6$=H and
$R^7$=substituted or unsubstituted phenyl, the radicals $R^1$ and $R^2$ do not together form a ring, provided that
(disclaimer group 2e) if $R^3$=substituted or unsubstituted thiophenyl, and $R^4$=—$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH^2$—$CH_2R^7$ or —$C(Y)$—$CH_2$—$CH_2$—$CH_2R^7$,
where $Y=H_2$
$R^6$=H and
$R^7$=substituted or unsubstituted aryl, the radicals $R^1$ and $R^2$ do not together form a ring, provided that
(disclaimer group 2f) if $R^3$=substituted or unsubstituted thiophenyl, and $R^4$=—$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH^2$—$CH_2R^7$ or —$C(Y)$—$CH_2$—$CH_2$—$CH_2R^7$
where $Y=H_2$
$R^6$=H, saturated or unsaturated, branched or unbranched, singly or multiply substituted or unsubstituted $C_{1-7}$-alkyl, and
$R^7$=substituted or unsubstituted aryl the radicals $R^1$ and $R^2$ do not together form a ring, provided that
(disclaimer group 2g) if $R^3$=substituted or unsubstituted heteroaryl, and $R^4$=—$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH^2$—$CH_2R^7$ or —$C(Y)$—$CH_2$—$CH_2$—$CH_2R^7$
where $Y=H_2$
$R^6$=H or saturated or unsaturated, branched or unbranched, singly or multiply substituted or unsubstituted $C_{1-7}$-alkyl, and
$R^7$=substituted or unsubstituted phenyl the radicals $R^1$ and $R^2$ do not together form a ring, or provided that
(disclaimer group 2h) if $R^3$=substituted or unsubstituted heteroaryl, and $R^4$=—$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH^2$—$CH_2R^7$ or —$C(Y)$—$CH_2$—$CH_2$—$CH_2R^7$
where $Y=H_2$
$R^6$=H, saturated or unsaturated, branched or unbranched, singly or multiply substituted or unsubstituted $C_{1-7}$-alkyl, and
$R^7$=substituted or unsubstituted aryl the radicals $R^1$ and $R^2$ do not together form a ring.

In the context of this invention, alkyl and cycloalkyl radicals are taken to mean saturated and unsaturated (but not aromatic), branched, unbranched and cyclic hydrocarbons which may be unsubstituted or singly or multiply substituted. In this case, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4 or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, C1–8-alkyl represents C1-, C2-, C3-, C4-, C5-, C6-, C7 or C8-alkyl, C1–10-alkyl represents C1-, C2-, C3-, C4-, C5-, C6-, C7-, C8-, C9- or C10-alkyl and C1–18-alkyl represents C1-, C2-, C3-, C4-, C5-, C6-, C7-, C8-, C9-, C10-, C11-, C12, C13, C14-, $C_{15}$-, C16-, $C_{17}$- or C18-alkyl. Furthermore, C3–4-cycloalkyl represents C3- or C4-cycloalkyl, C3–5-cycloalkyl represents C3-, C4- or C5-cycloalkyl, C3–6-cycloalkyl represents C3-, C4-, C5- or C6-cycloalkyl, C3–7-cycloalkyl represents C3-, C4-, C5-, C6- or C7-cycloalkyl, C3–8-cycloalkyl represents C3-, C4-, C5-, C6-, C7- or C8-cycloalkyl, C4–5-cycloalkyl represents C4- or C5-cycloalkyl, C4–6-cycloalkyl represents C4-, C5- or C6-cycloalkyl, C4–7-cycloalkyl represents C4-, C5-, C6- or C7-cycloalkyl, C5–6-cycloalkyl represents C5- or C6-cycloalkyl and C5–7-cycloalkyl represents C5-, C6- or C7-cycloalkyl. With respect to cycloalkyl, the term also comprises saturated cycloalkyls, in which one or two carbon atoms are replaced by a heteroatom, S, N or O. However, the term cycloalkyl also includes, in particular, singly or multiply, preferably singly, unsaturated cycloalkyls without a heteroatom in the ring, if the cycloalkyl is not an aromatic system. The alkyl and cycloalkyl radicals are preferably ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ and pyrazolinone, oxopyrazolinone, [1,4]dioxan or dioxolan.

In this case, in conjunction with alkyl and cycloalkyl—unless this is not explicitly defined otherwise—the term substituted in the context of this invention is taken to mean the substitution of at least one (optionally also more) hydrogen radical(s) by F, Cl, Br, I, $NH_2$, SH or OH, wherein "multiply substituted" or "substituted" with multiple substitution is taken to mean that the substitution is made both on different and on the same atoms multiply with the same or different substituents, for example threefold on the same carbon atom as in the case of $CF_3$ or at different points as in the case of —CH(OH)—CH═CH—$CHCl_2$. Particularly preferred substituents in this case are F, Cl and OH. With respect to cycloalkyl, the hydrogen radical can also be replaced by $OC_{1-3}$ alkyl or $C_{1-3}$ alkyl (singly or multiply substituted or unsubstituted respectively), in particular methyl, ethyl, n-propyl, i-propyl, $CF_3$, methoxy or ethoxy.

The term $(CH_2)_{3-6}$ is taken to mean —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is taken to mean —$CH_2$—, —$CH_2$—$CH_2$—, —$CH_2$—$CH_2$—$CH_2$— and —$CH_2$—

$CH_2$—$CH_2$—$CH_2$, $(CH_2)_{4-5}$ is taken to mean —$CH_2$—$CH_2$—$CH_2$—$CH_2$— and —$CH_2$—$CH_2$—$CH_2$—$CH_2$— etc.

An aryl radical is taken to mean ring systems with at least one aromatic ring but without heteroatoms in even only one of the rings. Examples are phenyl, naphthyl, fluoranthenyl, fluorenyl, tetralinyl or indanyl, in particular 9H fluorenyl or anthracenyl radicals which may be unsubstituted or singly or multiply substituted.

A heteroaryl radical is taken to mean heterocyclic ring systems with at least one unsaturated ring which contain one or more heteroatoms from the group comprising nitrogen, oxygen and/or sulfur and which can also be singly or multiply substituted. Examples from the group of heteroaryls include furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolan, benzodioxan, carbazole, indole and quinazoline.

In this case, in conjunction with aryl and heteroaryl, substituted is taken to mean the substitution of the aryl or heteroaryl by $R^{82}$, $OR^{82}$ a halogen, preferably F and/or Cl, a $CF_3$, a CN, a $NO_2$, a $NR^{83}R^{84}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

In this case the radical $R^{82}$ represents H, a $C_{1-10}$ alkyl, preferably a $C_{1-6}$ alkyl, an aryl or heteroaryl radical or an aryl or heteroaryl radical bound by saturated or unsaturated $C_{1-3}$ alkyl, or a $C_{1-3}$ alkylene-group-bound aryl or heteroaryl radical, wherein these aryl or heteroaryl radicals must not themselves be substituted by aryl or heteroaryl radicals, the radicals $R^{83}$ and $R^{84}$, which are the same or different, represent H, a $C_{1-10}$ alkyl, preferably a $C_{1-6}$ alkyl, an aryl radical, a heteroaryl radical or an aryl or heteroaryl radical bound by saturated or unsaturated $C_{1-3}$ alkyl or a $C_{1-3}$ alkylene-group-bound aryl or heteroaryl radical, wherein these aryl or heteroaryl radicals must not themselves be substituted by aryl or heteroaryl radicals, or the radicals $R^{83}$ and $R^{84}$ together represent $CH_2CH_2OCH_2CH_2$, $CH_2CH_2HR^{85}CH_2CH_2$ or $(CH_2)_{3-6}$, and the radical $R^{85}$ represents H, a $C_{1-10}$ alkyl, preferably a $C_{1-6}$ alkyl, an aryl radical, a heteroaryl radical or an aryl or heteroaryl radical bound by saturated or unsaturated $C_{1-3}$ alkyl or a $C_{1-3}$ alkylene-group-bound aryl or heteroaryl radical, wherein these aryl or heteroaryl radicals must not themselves be substituted by aryl or heteroaryl radicals.

The term salt is taken to mean any form of the active ingredient according to the invention in which it assumes or is charged with an ionic form and is coupled to a counter ion (a cation or anion) or is in solution. This also includes complexes of the active ingredient with other molecules and ions, in particular complexes complexed by ionic interactions. In particular, it includes (and this is also a preferred embodiment of this invention) physiologically acceptable salts, in particular physiologically acceptable salts with cations or bases and physiologically acceptable salts with anions or acids or also a salt formed with a physiologically acceptable acid or a physiologically acceptable cation.

The term physiologically acceptable is taken to mean that the substance, in particular the salt as such, is acceptable when used in humans or mammals, in other word, for example, is not non-physiological (for example toxic).

The term physiologically acceptable salts with anions or acids is taken to mean, in the context of this invention, salts of at least one of the compounds according to the invention—usually protonated, for example on nitrogen—as cation with at least one anion which are physiologically acceptable—in particular when applied to humans and/or mammals. In the context of this invention this is taken to mean, in particular, the salt formed with a physiologically acceptable acid, namely salts of the respective active ingredient with inorganic or organic acids which are physiologically acceptable—in particular when applied to humans and/or mammals. Examples of physiologically acceptable salts of certain acids are salts of: hydrochloric acid, hydrobromic acid, sulfuric acid, methane sulfonic acid, formic acid, acetic acid, oxalic acid, succinic acid, malic acid, tartaric acid, mandelic acid, fumaric acid, lactic acid, citric acid, glutamic acid, 1,1-dioxo-1,2, dihydro-1λ⁶-benzo[d] isothiazol-3-one (saccharic acid), monomethyl sebacic acid, 5-oxo-proline, hexane-1-sulfonic acid, nicotinic acid, 2-, 3- or 4-aminobenzoic acid, 2,4,6-trimethyl-benzoic acid, α-lipoic acid, acetyl glycine, acetyl salicylic acid, hippuric acid and/or aspartic acid. The hydrochloride salt is particularly preferred.

The term salt formed with a physiologically acceptable acid in the context of this invention is taken to mean salts of the respective active ingredient with inorganic or organic acids which are physiologically acceptable—in particular when applied to humans and/or mammals. The hydrochloride is particularly preferred. Examples of physiologically acceptable acids include: hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, 1,1-dioxo-1,2,dihydro-1λ⁶-benzo[d]isothiazol-3-one (saccharic acid), monomethyl sebacic acid, 5-oxo-proline, hexane-1-sulfonic acid, nicotinic acid, 2-, 3- or 4-aminobenzoic acid, 2,4,6-trimethyl-benzoic acid, α-lipoic acid, acetyl glycine, acetyl salicylic acid, hippuric acid and/or aspartic acid.

The term physiologically acceptable salts with cations or bases is taken to mean, in the context of this invention, salts of at least one of the compounds according to the invention—usually a (deprotonated) acid—as anion with at least one, preferably inorganic, cation which are physiologically acceptable, in particular when applied to humans and/or mammals. The salts of the alkali and alkaline earth metals, but also with $NH_4^+$ are particularly preferred, in particular however (mono) or (di) sodium, (mono) or (di) potassium, magnesium or calcium salts.

The term salt formed with a physiologically acceptable cation in the context of this invention is taken to mean salts with at least one of the respective compounds as anion with at least one inorganic cation which is physiologically acceptable—in particular when applied to humans and/or mammals. The salts of the alkali and alkaline earth metals, but also $NH_4^+$ are particularly preferred, in particular however (mono) or (di) sodium, (mono) or (di) potassium, magnesium or calcium salts.

The invention accordingly also relates to substituted 4-aminocyclohexanols described hereinafter as substance group A corresponding to formula I,

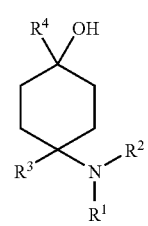

I wherein
the radicals $R^1$ and $R^2$ together form a ring and represent $CH_2CH_2OCH_2CH_2$, $CH_2CH_2NR^5CH_2CH_2$ or $(CH_2)_{3-6}$,
where $R^5$ is selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl;

$R^3$ is selected from respectively unsubstituted or singly or multiply substituted aryl or heteroaryl;

$R^4$ is selected from respectively unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$
where Y=O, S or $H_2$,
where $R^6$ is selected from
H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
and where $R^7$ is selected from
H; respectively unsubstituted or singly or multiply substituted $C_{3-8}$-cycloalkyl, aryl or heteroaryl,
where $R^8$ is selected from
respectively unsubstituted or singly or multiply substituted aryl or heteroaryl,
where L is selected from
—C(O)—NH—, —NH—C(O)—, —C(O)—O—, —O—C(O)—, —O—, —S— or —S(O)$_2$—
where $R^9$ is selected from
respectively unsubstituted or singly or multiply substituted aryl or heteroaryl, provided that,
(disclaimer group 2) if $R^3$=substituted or unsubstituted thiophenyl, and $R^4$=—$CH_2$—$CH_2$-phenyl
the radicals $R^1$ and $R^2$ do not together form a ring and represent $(CH_2)_5$, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

The invention accordingly also relates to substituted 4-aminocyclohexanols described hereinafter as substance group C corresponding to formula I,

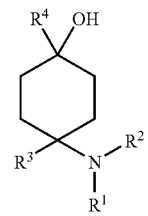

I wherein
$R^1$ and $R^2$ independently of one another are selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl; wherein $R^1$ and $R^2$ are not both H, $R^3$ is selected from respectively unsubstituted or singly or multiply substituted aryl or heteroaryl;

$R^4$ is selected from respectively unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$
where Y=O, S or $H_2$,
where $R^6$ is selected from
H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
and where $R^7$ is selected from
H; respectively unsubstituted or singly or multiply substituted $C_{3-8}$-cycloalkyl, aryl or heteroaryl,
where $R^8$ is selected from
respectively unsubstituted or singly or multiply substituted aryl or heteroaryl,
where L is selected from
—C(O)—NH—, —NH—C(O)—, —C(O)—O—, —O—C(O)—, —O—, —S— or —S(O)$_2$—
where $R^9$ is selected from
respectively unsubstituted or singly or multiply substituted aryl or heteroaryl, provided that,
(disclaimer group 1) if $R^3$=substituted or unsubstituted phenyl, and $R^4$=phenyl or —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$
where Y=$H_2$
$R^6$=H, saturated or unsaturated, branched or unbranched, singly or multiply substituted or unsubstituted $C_{1-5}$-alkyl, and/or
$R^7$=H, respectively substituted or unsubstituted $C_{3-8}$-cycloalkyl or phenyl,
$R^1$ and $R^2$ independently of one another are not both $C_{1-5}$-alkyl, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

The invention accordingly also relates to substituted 4-aminocyclohexanols described hereinafter as substance group D corresponding to formula I,

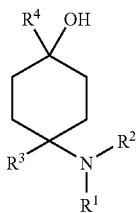

I wherein
R$^1$ and R$^2$ independently of one another are selected from H; respectively saturated or unsaturated, branched or unbranched, singly or multiply substituted or unsubstituted C$_{1-8}$-alkyl or C$_{3-8}$-cycloalkyl; respectively singly or multiply substituted or unsubstituted aryl or heteroaryl; or respectively singly or multiply substituted or unsubstituted aryl bound via C$_{1-3}$-alkylene, C$_{3-8}$-cycloalkyl or heteroaryl; wherein R$^1$ and R$^2$ may not both be H, or the radicals R$^1$ and R$^2$ together form a ring and represent CH$_2$CH$_2$OCH$_2$CH$_2$, CH$_2$CH$_2$NR$^5$CH$_2$CH$_2$ or (CH$_2$)$_{3-6}$,
  where R$^5$ is selected from H; respectively saturated or unsaturated, branched or unbranched, singly or multiply substituted or unsubstituted C$_{1-8}$-alkyl or C$_{3-8}$-cycloalkyl; respectively singly or multiply substituted or unsubstituted aryl or heteroaryl; or respectively singly or multiply substituted or unsubstituted aryl bound via C$_{1-3}$-alkylene, C$_{3-8}$-cycloalkyl or heteroaryl;
R$^3$ is selected from respectively unsubstituted or singly or multiply substituted heteroaryl;
R$^4$ is selected from respectively unsubstituted or singly or multiply substituted C$_{3-8}$-cycloalkyl, aryl or heteroaryl; —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$; or —R$^8$-L-R$^9$
  where Y=O, S or H$_2$,
  where R$^6$ is selected from
    H, saturated or unsaturated, branched or unbranched, singly or multiply substituted or unsubstituted C$_{1-7}$-alkyl; or saturated or unsaturated, branched or unbranched, singly or multiply substituted or unsubstituted C(O)O—C$_{1-6}$-alkyl;
  where R$^7$ is selected from
    H; respectively unsubstituted or singly or multiply substituted C$_{3-8}$-cycloalkyl, aryl or heteroaryl,
  where R$^8$ is selected from
    respectively unsubstituted or singly or multiply substituted aryl or heteroaryl,
  where L is selected from
    —C(O)—NH—, —NH—C(O)—, —C(O)—O—, —O—C(O)—, —O—, —S— or —S(O)$_2$—
  where R$^9$ is selected from
    respectively unsubstituted or singly or multiply substituted aryl or heteroaryl, provided that,
  (disclaimer group 2) if R$^3$=substituted or unsubstituted thiophenyl, and R$^4$=—CH$_2$—CH$_2$-phenyl the radicals R$^1$ and R$^2$ do not together form a ring and represent (CH$_2$)$_5$, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

The invention accordingly also relates to substituted 4-aminocyclohexanols described hereinafter as substance group E corresponding to formula I,

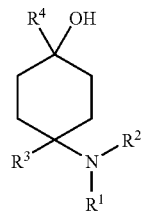

I wherein
R$^1$ and R$^2$ independently of one another are selected from H; respectively saturated or unsaturated, branched or unbranched, singly or multiply substituted or unsubstituted C$_{1-8}$-alkyl or C$_{3-8}$-cycloalkyl; respectively singly or multiply substituted or unsubstituted aryl or heteroaryl; or respectively singly or multiply substituted or unsubstituted aryl bound via C$_{1-3}$-alkylene, C$_{3-8}$-cycloalkyl or heteroaryl; wherein R$^1$ and R$^2$ may not both be H,
or the radicals R$^1$ and R$^2$ together form a ring and represent CH$_2$CH$_2$OCH$_2$CH$_2$, CH$_2$CH$_2$NR$^5$CH$_2$CH$_2$ or (CH$_2$)$_{3-6}$,
  where R$^5$ is selected from H; respectively saturated or unsaturated, branched or unbranched, singly or multiply substituted or unsubstituted C$_{1-8}$-alkyl or C$_{3-8}$-cycloalkyl; respectively singly or multiply substituted or unsubstituted aryl or heteroaryl; or respectively singly or multiply substituted or unsubstituted aryl bound via C$_{1-3}$-alkylene, C$_{3-8}$-cycloalkyl or heteroaryl;
R$^3$ is selected from unsubstituted or singly or multiply substituted aryl;
R$^4$ is selected from respectively unsubstituted or singly or multiply substituted C$_{3-8}$-cycloalkyl, aryl or heteroaryl; —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—H$_2$—CH$_2$R$^7$ or —C(Y)—CH$_2$—CH$_2$—CH$_2$R$^7$; or —R$^8$-L-R$^9$
  ere Y=O, S or H$_2$, where $R^6$ is selected from
  H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
where $R^7$ is selected from
  H; respectively unsubstituted or singly or multiply substituted $C_{3-8}$-cycloalkyl, aryl or heteroaryl,
where $R^8$ is selected from
  respectively unsubstituted or singly or multiply substituted aryl or heteroaryl,
where L is selected from
  —C(O)—NH—, —NH—C(O)—, —C(O)—O—, —O—C(O)—, —O—, —S— or —S(O)$_2$—
where $R^9$ is selected from
  respectively unsubstituted or singly or multiply substituted aryl or heteroaryl, provided that,
  (disclaimer group 1) if $R^3$=substituted or unsubstituted phenyl, and $R^4$=phenyl or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$
    where Y=H$_2$
    $R^6$=H, saturated or unsaturated, branched or unbranched, singly or multiply substituted or unsubstituted $C_{1-5}$-alkyl, and/or
    $R^7$=H, respectively substituted or unsubstituted $C_{3-8}$-cycloalkyl or phenyl,
  $R^1$ and $R^2$ independently of one another are not both $C_{1-5}$-alkyl, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

The invention accordingly also relates to substituted 4-aminocyclohexanols described hereinafter as substance group F corresponding to formula I,

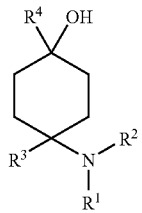

wherein
  the radicals $R^1$ and $R^2$ together form a ring and represent CH$_2$CH$_2$OCH$_2$CH$_2$, CH$_2$CH$_2$NR$^5$CH$_2$CH$_2$ or (CH$_2$)$_{3-6}$,
    where $R^5$ is selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl;
  $R^3$ is selected from respectively unsubstituted or singly or multiply substituted aryl;
  $R^4$ is selected from respectively unsubstituted or singly or multiply substituted $C_{3-8}$-cycloalkyl, aryl or heteroaryl; —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$; or —R$^8$-L-R$^9$
    where Y=O, S or H$_2$,
  where $R^6$ is selected from
    H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
  and where $R^7$ is selected from
    H; respectively unsubstituted or singly or multiply substituted $C_{3-8}$-cycloalkyl, aryl or heteroaryl,
  where $R^8$ is selected from
    respectively unsubstituted or singly or multiply substituted aryl or heteroaryl,
  where L is selected from
    —C(O)—NH—, —NH—C(O)—, —C(O)—O—, —O—C(O)—, —O—, —S— or —S(O)$_2$—
  where $R^9$ is selected from
    respectively unsubstituted or singly or multiply substituted aryl or heteroaryl, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

The invention accordingly also relates to substituted 4-aminocyclohexanols described hereinafter as substance group F corresponding to formula I,

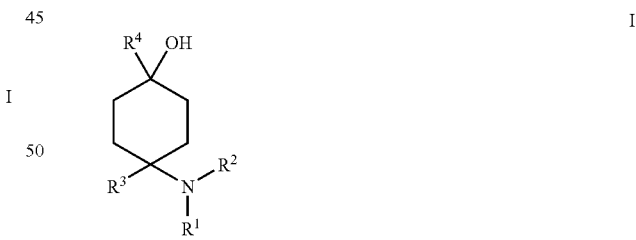

wherein
  $R^1$ and $R^2$ independently of one another are selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl; wherein $R^1$ and $R^2$ are not both H,
  $R^3$ is selected from unsubstituted or singly or multiply substituted heteroaryl;

$R^4$ is selected from respectively unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$ where Y=O, S or $H_2$, where $R^6$ is selected from H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;

where $R^7$ is selected from

H; respectively unsubstituted or singly or multiply substituted $C_{3-8}$-cycloalkyl, aryl or heteroaryl, where $R^8$ is selected from respectively unsubstituted or singly or multiply substituted aryl or heteroaryl, where L is selected from —C(O)—NH—, —NH—C(O)—, —C(O)—O—, —O—C(O)—, —O—, —S— or —S(O)$_2$— where $R^9$ is selected from respectively unsubstituted or singly or multiply substituted aryl or heteroaryl, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

The invention accordingly also relates to substituted 4-aminocyclohexanols described hereinafter as substance group H corresponding to formula I,

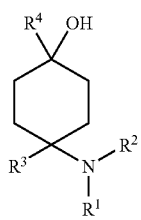

I wherein $R^1$ and $R^2$ independently of one another are selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl; wherein $R^1$ and $R^2$ are not both H, or the radicals $R^1$ and $R^2$ together form a ring and represent $CH_2CH_2OCH_2CH_2$, $CH_2CH_2NR^5CH_2CH_2$ or $(CH_2)_{3-6}$, where $R^5$ is selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl;

$R^3$ is selected from respectively unsubstituted or singly or multiply substituted aryl or heteroaryl;

$R^4$ is selected from respectively unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$ where Y=$H_2$, where $R^6$ is selected from H, saturated or unsaturated, branched or unbranched, singly or multiply substituted or unsubstituted $C_{1-7}$-alkyl and where $R^7$ is selected from respectively unsubstituted or singly or multiply substituted heteroaryl, where $R^8$ is selected from respectively unsubstituted or singly or multiply substituted aryl or heteroaryl, where L is selected from —C(O)—NH—, —NH—C(O)—, —C(O)—O—, —O—C(O)—, —O—, —S— or —S(O)$_2$— where $R^9$ is selected from respectively unsubstituted or singly or multiply substituted aryl or heteroaryl, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

The invention accordingly also relates to substituted 4-aminocyclohexanols described hereinafter as substance group J corresponding to formula I,

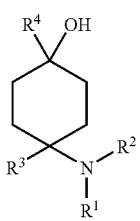

wherein $R^1$ and $R^2$ independently of one another are selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl; wherein $R^1$ and $R^2$ are not both H, or the radicals $R^1$ and $R^2$ together form a ring and represent $CH_2CH_2OCH_2CH_2$, $CH_2CH_2NR^5CH_2CH_2$ or $(CH_2)_{3-6}$, where $R^5$ is selected from H; respectively saturated or unsaturated, branched or unbranched, singly or multiply substituted or unsubstituted $C_{1-8}$-alkyl or $C_{3-8}$-cycloalkyl;
respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl;
$R^3$ is selected from respectively unsubstituted or singly or multiply substituted aryl or heteroaryl;
$R^4$ is selected from —$CHR^6R^7$, —$CHR^6$—$CH_2R^7$, —$CHR^6$—$CH_2$—$CH_2R^7$ or —$CHR^6$—$CH_2$—$CH_2$—$CH_2R^7$,
where $R^6$ is selected from
or saturated or unsaturated, branched or unbranched, singly or multiply substituted or unsubstituted $C(O)O$—$C_{1-6}$-alkyl;
and where $R^7$ is selected from
H; respectively unsubstituted or singly or multiply substituted $C_{3-8}$-cycloalkyl, aryl or heteroaryl, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

The invention accordingly also relates to substituted 4-aminocyclohexanols described hereinafter as substance group K corresponding to formula I,

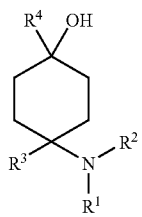

I wherein
$R^1$ and $R^2$ independently of one another are selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl; wherein $R^1$ and $R^2$ are not both H,
or the radicals $R^1$ and $R^2$ together form a ring and represent $CH_2CH_2OCH_2CH_2$, $CH_2CH_2NR^5CH_2CH_2$ or $(CH_2)_{3-6}$,
where $R^5$ is selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl;
$R^3$ is selected from respectively unsubstituted or singly or multiply substituted aryl or heteroaryl;

$R^4$ is selected from —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$;
where Y=O or S,
where $R^7$ is selected from
H; respectively unsubstituted or singly or multiply substituted $C_{3-8}$-cycloalkyl, aryl or heteroaryl, optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

With respect to substance groups A, D, E, H, J or K, it is preferred if
$R^1$ and $R^2$ independently of one another are selected from H; saturated or unsaturated, branched or unbranched, singly or multiply substituted or unsubstituted $C_{1-8}$-alkyl; wherein $R^1$ and $R^2$ are not both H,
or the radicals $R^1$ and $R^2$ together form a ring and represent $CH_2CH_2OCH_2CH_2$, $CH_2CH_2NR^5CH_2CH_2$ or $(CH_2)_{3-6}$,
where $R^5$ is selected from H; saturated or unsaturated, branched or unbranched, singly or multiply substituted or unsubstituted $C_{1-8}$-alkyl,
preferably
$R^1$ and $R^2$ independently of one another are selected from H; saturated or unsaturated, branched or unbranched, singly or multiply substituted or unsubstituted $C_{1-4}$-alkyl; wherein $R^1$ and $R^2$ are not both H,
or the radicals $R^1$ and $R^2$ together form a ring and represent $(CH_2)_{4-5}$,
in particular
$R^1$ and $R^2$ independently of one another are selected from methyl or ethyl or the radicals $R^1$ and $R^2$ together form a ring and represent $(CH_2)_5$.

With respect to substance group C or G, it is preferred if
$R^1$ and $R^2$ independently of one another are selected from H; saturated or unsaturated, branched or unbranched, singly or multiply substituted or unsubstituted $C_{1-8}$-alkyl; wherein $R^1$ and $R^2$ are not both H,
preferably
$R^1$ and $R^2$ independently of one another are selected from H; saturated or unsaturated, branched or unbranched, singly or multiply substituted or unsubstituted $C_{1-4}$-alkyl; wherein $R^1$ and $R^2$ are not both H,
in particular
$R^1$ and $R^2$ independently of one another are selected from methyl or ethyl.

With respect to substance group B or F, it is preferred if
$R^1$ and $R^2$ together form a ring and represent $CH_2CH_2OCH_2CH_2$, $CH_2CH_2NR^5CH_2CH_2$ or $(CH_2)_{3-6}$,
where $R^5$ is selected from H; saturated or unsaturated, branched or unbranched, singly or multiply substituted or unsubstituted $C_{1-8}$-alkyl,
preferably
$R^1$ and $R^2$ together form a ring and represent $(CH_2)_{4-5}$,
in particular
$R^1$ and $R^2$ together form a ring and represent $(CH_2)_5$.

With respect to substance groups A, B, C, H, J or K, it is preferred if
$R^3$ is selected from respectively unsubstituted or singly or multiply substituted phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl;
preferably
$R^3$ is selected from respectively unsubstituted or singly or multiply substituted phenyl, thiophenyl, pyridyl, furyl, benzofuranyl, benzodioxolanyl, indolyl, indanyl, benzodioxanyl, pyrrolyl, pyrimidyl or pyrazinyl;
in particular
$R^3$ is selected from respectively unsubstituted or singly or multiply substituted phenyl, pyridyl, furyl or thiophenyl.

With respect to substance groups D or G, it is preferred if
$R^3$ is selected from respectively unsubstituted or singly or multiply substituted thiophenyl, benzothiophenyl, pyridyl, furyl, benzofuranyl, benzodioxolanyl, indolyl, indanyl, benzodioxanyl, pyrrolyl, pyrimidyl or pyrazinyl;
preferably
$R^3$ is selected from respectively unsubstituted or singly or multiply substituted thiophenyl, pyridyl, furyl, benzofuranyl, benzodioxolanyl, indolyl, indanyl, benzodioxanyl, pyrrolyl, pyrimidyl or pyrazinyl;
in particular
$R^3$ is selected from respectively unsubstituted or singly or multiply substituted pyridyl, furyl or thiophenyl.

With respect to substance groups E or F, it is preferred if
$R^3$ is selected from phenyl, naphthyl, anthracenyl;
preferably
$R^3$ is selected from respectively unsubstituted or singly or multiply substituted phenyl or naphthyl;
in particular
$R^3$ is selected from unsubstituted or singly or multiply substituted phenyl.

With respect to substance groups A to G, it is preferred if
$R^4$ is selected from respectively unsubstituted or singly or multiply substituted $C_{3-8}$-cycloalkyl, aryl or heteroaryl; or —$R^8$-L-$R^9$
preferably
$R^4$ is selected from respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl; or —$R^8$-L-$R^9$
in particular
$R^4$ is selected from respectively unsubstituted or singly or multiply substituted cyclopentyl, cyclohexyl, cycloheptyl, cyclooctyl, anthracenyl, indolyl, naphthyl, benzofuranyl, benzothiazolyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl; or —$R^8$-L-$R^9$.

With respect to the foregoing embodiment, it is also preferred if
$R^8$ is selected from
respectively unsubstituted or singly or multiply substituted indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl,
L is selected from
—C(O)—NH—, —NH—C(O)—, —C(O)—O—, —O—C(O)—, —O—, —S— or —S(O)$_2$—,
and/or $R^9$ is selected from
respectively unsubstituted or singly or multiply substituted indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl, preferably
$R^8$ is selected from
respectively unsubstituted or singly or multiply substituted indolyl, benzothiophenyl, phenyl, thiophenyl, furyl, pyridyl, pyrrolyl, pyrazinyl or pyrimidyl,
L is selected from
—C(O)—NH—, —NH—C(O)—, —C(O)—O—, —O—C(O)— or —S(O)$_2$—,
and/or $R^9$ is selected from
respectively unsubstituted or singly or multiply substituted indolyl, benzothiophenyl, phenyl, thiophenyl, furyl, pyridyl, pyrrolyl, pyrazinyl or pyrimidyl, in particular
$R^8$ is selected from
unsubstituted indolyl,
L is selected from
—S(O)$_2$
and $R^9$ is selected from
unsubstituted phenyl.

With respect to substance groups A to G, it is also a preferred embodiment if
$R^4$ is selected from —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$
where Y=O, S or H$_2$, preferably
$R^4$ is selected from —CHR$^6$R$^7$, —CHR$^6$—CH$_2$R$^7$, —CHR$^6$—CH$_2$—CH$_2$R$^7$, —C(Y)R$^7$, —C(Y)—CH$_2$R$^7$ or —C(Y)—CH$_2$—CH$_2$R$^7$
where Y=O or S, in particular
$R^4$ is selected from —CHR$^6$R$^7$, —CHR$^6$—CH$_2$R$^7$, —C(Y)R$^7$ or —C(Y)—CH$_2$R$^7$
where Y=O.

With respect to the foregoing embodiment, it is also preferred if
$R^6$ is selected from
H, saturated or unsaturated, branched or unbranched, singly or multiply substituted or unsubstituted $C_{1-4}$-alkyl; or saturated or unsaturated, branched or unbranched, singly or multiply substituted or unsubstituted C(O)O—$C_{1-4}$-alkyl;
preferably
H, saturated or unsaturated, branched or unbranched, singly or multiply substituted or unsubstituted $C_{1-4}$-alkyl;
in particular
H, $CH_3$ and $C_2H_5$.

With respect to the foregoing embodiment, it is also preferred if
$R^7$ is selected from respectively unsubstituted or singly or multiply substituted $C_{3-8}$-cycloalkyl, aryl or heteroaryl;
preferably
$R^7$ is selected from respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl;
in particular
$R^7$ is selected from respectively unsubstituted or singly or multiply substituted cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl.

With respect to substance group H, it is a preferred embodiment if
$R^4$ is selected from respectively unsubstituted or singly or multiply substituted heteroaryl; or —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$
where Y=$H_2$,
preferably
$R^4$ is selected from respectively unsubstituted or singly or multiply substituted indolyl, benzofuranyl, benzothiophenyl, indanyl, benzodioxanyl, benzodioxolanyl, acenaphthyl, carbazolyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl;
or —CHRR, —CHR—$CH_2$R, —CHR—$CH_2$—$CH_2$R, —C(Y)R, —C(Y)—$CH_2$R or —C(Y)—$CH_2$—$CH_2$R
where Y=$H_2$,
in particular
$R^4$ is selected from respectively unsubstituted or singly or multiply substituted indolyl, benzofuranyl, benzothiophenyl, benzothiazolyl, indanyl, benzodioxanyl, benzodioxolanyl, acenaphthyl, carbazolyl, thiophenyl, furyl, pyridyl, pyrrolyl, pyrazinyl or pyrimidyl; or —$CHR^6R^7$, —$CHR^6$—$CH_2R^7$, —$C(Y)R^7$ or —$C(Y)$—$CH_2R^7$,
where Y=$H_2$.

With respect to the foregoing embodiment, it is also preferred if
$R^6$ is selected from
H, saturated or unsaturated, branched or unbranched, singly or multiply substituted or unsubstituted $C_{1-4}$-alkyl;
preferably
H, saturated or unsaturated, branched or unbranched, singly or multiply substituted or unsubstituted $C_{1-4}$-alkyl;
in particular
H, $CH_3$ and $C_2H_5$
and/or
$R^7$ is selected from respectively unsubstituted or singly or multiply substituted indolyl, benzofuranyl, benzothiophenyl, indanyl, benzodioxanyl, benzodioxolanyl, acenaphthyl, carbazolyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl;
preferably
$R^7$ is selected from respectively unsubstituted or singly or multiply substituted indolyl, benzofuranyl, benzothiophenyl, indanyl, benzodioxanyl, benzodioxolanyl, acenaphthyl, carbazolyl, thiophenyl, furyl, pyridyl, pyrrolyl, pyrazinyl or pyrimidyl;
in particular
$R^7$ is selected from respectively unsubstituted or singly or multiply substituted thiophenyl, furyl, pyridyl, pyrrolyl, pyrazinyl or pyrimidyl.

With respect to the foregoing embodiment, it is also preferred if
$R^8$ is selected from
respectively unsubstituted or singly or multiply substituted indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl,
L is selected from
—C(O)—NH—, —NH—C(O)—, —C(O)—O—, —O—C(O)—, —O—, —S— or —$S(O)_2$—,
and/or $R^9$ is selected from
respectively unsubstituted or singly or multiply substituted indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl,
preferably
$R^8$ is selected from
respectively unsubstituted or singly or multiply substituted indolyl, benzothiophenyl, phenyl, thiophenyl, furyl, pyridyl, pyrrolyl, pyrazinyl or pyrimidyl,
L is selected from
—C(O)—NH—, —NH—C(O)—, —C(O)—O—, —O—C(O)— or —$S(O)_2$—,
and/or $R^9$ is selected from respectively unsubstituted or singly or multiply substituted indolyl, benzothiophenyl, phenyl, thiophenyl, furyl, pyridyl, pyrrolyl, pyrazinyl or pyrimidyl, in particular
$R^8$ is selected from
unsubstituted indolyl,
L is selected from
—S(O)$_2$—
and R is selected from
unsubstituted phenyl.

With respect to substance group J, it is a preferred embodiment if
$R^4$ is selected from —CHR$^6$R$^7$, —CHR$^6$—CH$_2$R$^7$ or —CHR$^6$—CH$_2$—CH$_2$R$^7$
preferably
$R^4$ is selected from —CHR$^6$R$^7$ or —CHR$^6$—CH$_2$R$^7$,
in particular
$R^4$ is selected from —CHR$^6$R$^7$.

With respect to the foregoing embodiment, it is also preferred if
$R^6$ is selected from
saturated or unsaturated, branched or unbranched, singly or multiply substituted or unsubstituted C(O)O—C$_{1-4}$-alkyl;
preferably
saturated or unsaturated, branched or unbranched, singly or multiply substituted or unsubstituted C(O)O—C$_{1-3}$-alkyl;
in particular
C(O)O—CH$_3$ and C(O)O—C$_2$H$_5$
and/or
$R^7$ is selected from respectively unsubstituted or singly or multiply substituted C$_{3-8}$-cycloalkyl, aryl or heteroaryl;
preferably
$R^7$ is selected from respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl;
in particular
$R^7$ is selected from respectively unsubstituted or singly or multiply substituted cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl,.

With respect to substance group K, it is a preferred embodiment if
$R^4$ is selected from —C(Y)R$^7$, —C(Y)—CH$_2$R$^7$, —C(Y)CH$^2$—CH$_2$R$^7$ or —C(Y)—CH$_2$—CH$_2$—CH$_2$R$^7$
where Y=O
preferably
$R^4$ is selected from —C(Y)R$^7$, —C(Y)—CH$_2$R$^7$ or —C(Y)—CH$_2$—CH$_2$R$^7$,
where Y=O
in particular
$R^4$ is selected from —C(Y)R$^7$ or —C(Y)—CH$_2$R$^7$,
where Y=O.

With respect to the foregoing embodiment, it is also preferred if
$R^7$ is selected from respectively unsubstituted or singly or multiply substituted C$_{3-8}$-cycloalkyl, aryl or heteroaryl;
preferably
$R^7$ is selected from respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl;
in particular
$R^7$ is selected from respectively unsubstituted or singly or multiply substituted cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl.

In a preferred embodiment of all the aforementioned substance groups, the substituted 4-aminocyclohexanols according to the invention are selected from the following group:
4-dimethylamino-1-phenethyl-4-phenylcyclohexanol as well as the corresponding hydrochloride,
4-(4-chlorophenyl)-4-dimethylamino-1-phenethylcyclohexanol as well as the corresponding hydrochloride,
4-(4-bromophenyl)-4-dimethylamino-1-phenethylcyclohexanol as well as the corresponding hydrochloride,
4-dimethylamino-1-(1-methyl-1H-indol-2-yl)-4-phenylcyclohexanol
1-benzo[b]thiophen-2-yl-4-dimethylamino-4-phenylcyclohexanol
1-benzo[b]thiophen-3-yl-4-dimethylamino-4-phenylcyclohexanol
1-(1-benzenesulphonyl-1H-indol-2-yl)-4-dimethylamino-4-phenylcyclohexanol
1-benzofuran-2-yl-4-dimethylamino-4-phenylcyclohexanol
1-benzothiazol-2-yl-4-dimethylamino-4-phenylcyclohexanol optionally in the form of their racemates, their pure stereoisomers, in particular enantiomers or diastereomers, or in the form of mixtures of stereoisomers, in particular the enantiomers or diastereomers, in any mixing ratio; in the prepared form or in the form of their acids or bases or in the form of their salts, in particular the physiologically acceptable salts or in the form of their solvates, in particular the hydrates.

The substances according to the invention are toxicologically safe, so they are suitable as a pharmaceutical active ingredient.

The invention therefore also relates to pharmaceutical compositions containing at least one substituted 4-aminocyclohexanol according to the invention, optionally in the form of its racemate, the pure stereoisomers, in particular enantiomers or diastereomers, or in the form of mixtures of stereoisomers, in particular enantiomers or diastereomers, in any mixing ratio; in the prepared form or in the form of the acids or bases or in the form of the salts, in particular the physiologically acceptable salts or in the form of their solvates, in particular the hydrates; as well as optionally suitable additives and/or auxiliaries and/or optionally further active ingredients.

The pharmaceutical compositions according to the invention contain, in addition to at least one substituted 4-aminocyclohexanol compound according to the invention, optionally suitable additives and/or auxiliary agents, therefore also excipients, fillers, solvents, diluents, dyes and/or binders and can be administered as liquid pharmaceutical preparations in the form of injection solutions, drops or syrups, as semi-solid pharmaceutical preparations in the form of granules, tablets, pellets, patches, capsules, plasters or aerosols. The choice of auxiliary agents, etc. and the quantities thereof to be used depend on whether the pharmaceutical preparation is to be applied orally, perorally, parenterally, intravenously, intraperitoneally, intradermally, intramuscularly, intranasally, buccally, rectally or topically, for example to the skin, the mucus membranes or the eyes. Preparations in the form of tablets, dragees, capsules, granules, drops and syrups are suitable for oral application, solutions, suspensions, easily reconstitutable dry preparations and sprays are suitable for parenteral, topical and inhalative applications. Substituted 4-aminocyclohexanol compounds according to the invention in a deposit, in dissolved form or in a plaster, optionally with the addition of agents to promote skin penetration, are suitable percutaneous application preparations. Orally or percutaneously applicable preparation forms can release the substituted 4-aminocyclohexanol compound according to the invention after a delay. In principle, other active ingredients known to the person skilled in the art can be added to the pharmaceutical preparations according to the invention.

The quantity of active ingredient to be administered to the patient varies as a function of the weight of the patient, the method of application, the indication and the severity of the illness. Conventionally, 0.005 to 1,000 mg/kg, preferably 0.05 to 5 mg/kg of at least one substituted 4-aminocyclohexanol compound according to the invention are applied.

It is particularly preferred for all the aforementioned forms of the pharmaceutical composition according to the invention if, in addition to at least one substituted 4-aminocyclohexanol, the pharmaceutical composition also contains an opioid, preferably a strong opioid, in particular morphine, or an anesthetic, preferably hexobarbital or halothane.

In a preferred form of the pharmaceutical composition, a contained substituted 4-aminocyclohexanol according to the invention is present as a pure diastereomer and/or enantiomer, as a racemate or as a non-equimolar or equimolar blend of the diastereomers and/or enantiomers.

As mentioned in the introduction regarding the prior art, the ORL1 receptor has been identified, in particular in the event of pain. Substituted 4-aminocyclohexanol compounds according to the invention may accordingly be used to produce a pharmaceutical composition for the treatment of pain, in particular acute, visceral, neuropathic or chronic pain.

The invention therefore also relates to the use of a substituted 4-aminocyclohexanol compound corresponding to formula I, optionally in the form of its racemate, the pure stereoisomers, in particular enantiomers or diastereomers, or in the form of mixtures of stereoisomers, in particular enantiomers or diastereomers, in any mixing ratio; in the prepared form or in the form of the acids or bases or in the form of the salts, in particular the physiologically acceptable salts or in the form of the solvates, in particular the hydrates; for producing a pharmaceutical composition for the treatment of pain, in particular of acute, visceral, neuropathic or chronic pain.

As already mentioned in the introduction, the ORL1 receptor also plays a part in a large number of other physiological processes, in particular those of medical significance, in addition to its role in the event of pain.

The invention accordingly also relates to the use of a substituted 4-aminocyclohexanol compound corresponding to general formula I,

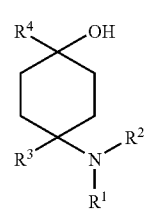

wherein
$R^1$ and $R^2$ independently of one another are selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl; wherein $R^1$ and $R^2$ are not both H,
or the radicals $R^1$ and $R^2$ together form a ring and represent $CH_2CH_2OCH_2CH_2$, $CH_2CH_2NR^5CH_2CH_2$ or $(CH_2)_{3-6}$,
where $R^5$ is selected from H; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted alkylene aryl bound via $C_{1-3}$, $C_{3-8}$-cycloalkyl or heteroaryl;
$R^3$ is selected from respectively unsubstituted or singly or multiply substituted aryl or heteroaryl;
$R^4$ is selected from respectively unsubstituted or singly or multiply substituted $C_{3-8}$-cycloalkyl, aryl or heteroaryl; —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$; or —R$^8$-L-R$^9$
where Y=O, S or H$_2$,
where $R^6$ is selected from
H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
where $R^7$ is selected from
H; respectively unsubstituted or singly or multiply substituted $C_{3-8}$-cycloalkyl, aryl or heteroaryl,
where $R^8$ is selected from
respectively unsubstituted or singly or multiply substituted aryl or heteroaryl,
where L is selected from
—C(O)—NH—, —NH—C(O)—, —C(O)—O—, —O—C(O)—, —O—, —S— or —S(O)$_2$— where $R^9$ is selected from
respectively unsubstituted or singly or multiply substituted aryl or heteroaryl, optionally in the form of its racemate, the pure stereoisomers, in particular enantiomers or diastereomers, or in the form of mixtures of stereoisomers, in particular enantiomers or diastereomers, in any mixing ratio; in the prepared form or in the form of the acids or bases or in the form of the salts, in particular the physiologically acceptable salts or in the form of the solvates, in particular the hydrates; for producing a pharmaceutical composition for the treatment of phobias, stress and syndromes associated with stress, depression, epilepsy, Alzheimer's disease, senile dementia, general cognitive dysfunction, learning difficulties and memory loss (as a nootropic), withdrawal symptoms, alcohol and/or drug and/or medicine abuse and/or dependency, sexual dysfunction, cardiovascular diseases, hypotension, hypertension, tinnitus, pruritus, migraine, defective hearing, defective bowel motility, impaired assimilation of food, anorexia, obesity, locomotive disorders, diarrhoea, cachexia, urinary incontinence or as a muscle relaxant, anticonvulsant, antitussive or anaesthetic or for co-administration during treatment with an opioid analgesic or with an anaesthetic, for diuresis or antinatriuresis and/or anxiolysis.

It may be preferred in one of the aforementioned uses if a substituted 4-aminocyclohexanol is in the form of a pure diastereomer and/or enantiomer, as a racemate or as a non-equimolar or equimolar blend of the diastereomers and/or enantiomers and/or, in addition to the substituted 4-aminocyclohexanol, also contains an opioid, preferably a strong opioid, in particular morphine, or an anesthetic, preferably hexobarbital or halothane.

The invention also relates to a method of treating, in particular in one of the aforementioned indications, a non-human mammal or human which or who requires treatment for pain, in particular chronic pain, by administration of a therapeutically effective dose of a substituted 4-aminocyclohexanol or of a pharmaceutical composition according to the invention.

The invention also relates to a method for producing the substituted 4-aminocyclohexanols according to the invention, as stated in the following description and examples.

A method comprising the following steps is particularly suitable:

a. a cyclohexane-1,4-dione protected by the groups $S^1$ and $S^2$ according to formula II is reacted in the presence of a compound of formula $HNR^{O1}R^{O2}$ with a cyanide, preferably potassium cyanide, to form a protected N-substituted 1-amino-4-oxo-cyclohexanecarbonitrile compound corresponding to formula III;

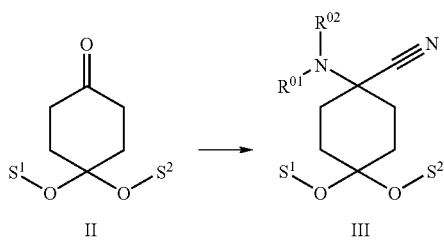

optionally, the compound is then acylated, alkylated or sulfonated in any sequence and optionally repeatedly and/or, in the case of compounds where $R^{O1}$ and/or $R^{O2}$ and/or $R^6$=H protected by a protective group, a protective group is removed at least once and optionally acylated, alkylated or sulfonated and/or, in the case of a compound where $R^{O1}$ and/or $R^{O2}$ and/or $R^6$=H, a protective group is introduced at least once and optionally acylated, alkylated or sulfonated, b. the aminonitrile according to formula III is reacted with organometallic reagents, preferably Grignard or organolithium reagents, having the formula metal-$R^3$ to form a compound according to formula IVa;

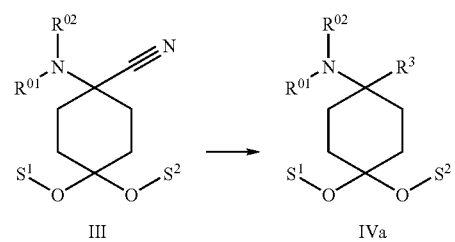

optionally, the compound is then acylated, alkylated or sulfonated in any sequence and optionally repeatedly and/or, in the case of compounds where $R^{O1}$ and/or $R^{O2}$ and/or $R^6$=H protected by a protective group, a protective group is removed at least once and optionally acylated, alkylated or sulfonated and/or, in the case of a compound where $R^{O1}$ and/or $R^{O2}$ and/or $R^6$=H, a protective group is introduced at least once and optionally acylated, alkylated or sulfonated, c. the protective groups $S^1$ and $S^2$ are removed according to formula III on the compound according to formula IVa to form a 4-substituted 4-aminocyclohexanone compound according to formula IV;

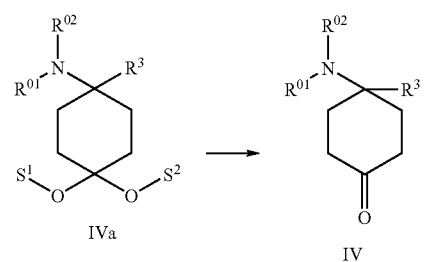

optionally, the compound is then acylated, alkylated or sulfonated in any sequence and optionally repeatedly and/or, in the case of compounds where $R^1$ and/or $R^{O2}$ and/or $R^6$=H protected by a protective group, a protective group is removed at least once and optionally acylated, alkylated or sulfonated and/or, in the case of a compound where $R^{O1}$ and/or $R^{O2}$ and/or $R^6$=H, a protective group is introduced at least once and optionally acylated, alkylated or sulfonated, d. the 4-substituted 4-aminocyclohexanone compound according to formula IV is reacted with organometallic reagents, preferably Grignard or organolithium reagents, having the formula metal-$R^{O4}$ to form a compound according to formula V;

optionally, the compound is then acylated, alkylated or sulfonated in any sequence and optionally repeatedly and/or, in the case of compounds where $R^{01}$ and/or $R^{02}$ and/or $R^{04}$ and/or $R^{05}$ and/or $R^6$=H protected by a protective group, a protective group is removed at least once and optionally acylated, alkylated or sulfonated and/or, in the case of a compound where $R^{01}$ and/or $R^{02}$ and/or $R^{04}$ and/or $R^{05}$ and/or $R^6$=H, a protective group is introduced at least once and optionally acylated, alkylated or sulfonated, wherein $R^1$, $R^2$, $R^3$ and $R^4$ have the meaning given in claim 1 and $R^{01}$ and $R^{02}$ independently of one another are selected from H; H provided with a protective group; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl;

or the radicals $R^{01}$ and $R^{02}$ together form a ring and represent $CH_2CH_2OCH_2CH_2$, $CH_2CH_2NR^{05}CH_2CH_2$ or $(CH_2)_{3-6}$, where $R^{05}$ is selected from H; H provided with a protective group; respectively saturated or unsaturated, branched or unbranched, singly or multiply substituted or unsubstituted $C_{1-8}$-alkyl or $C_{3-8}$-cycloalkyl; respectively singly or multiply substituted or unsubstituted aryl or heteroaryl; or respectively singly or multiply substituted or unsubstituted aryl bound via $C_{1-3}$-alkylene, $C_{3-8}$-cycloalkyl or heteroaryl;

$R^{04}$ is selected from H, H provided with a protective group; respectively unsubstituted or singly or multiply substituted $C_{3-8}$-cycloalkyl, aryl or heteroaryl; —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$; or —R$^8$-L-R$^9$ where Y=O, S or H$_2$, where $R^6$ is selected from H, saturated or unsaturated, branched or unbranched, singly or multiply substituted or unsubstituted $C_{1-7}$-alkyl;

and where $R^7$ is selected from

H; respectively unsubstituted or singly or multiply substituted $C_{3-8}$-cycloalkyl, aryl or heteroaryl, where $R^8$ is selected from respectively unsubstituted or singly or multiply substituted aryl or heteroaryl, where L is selected from —C(O)—NH—, —NH—C(O)—, —C(O)—O—, —O—C(O)—, —O—, —S— or —S(O)$_2$— where $R^9$ is selected from respectively unsubstituted or singly or multiply substituted aryl or heteroaryl, and $S^1$ and $S^2$ independently of one another are selected from protective groups or together represent a protective group, preferably monoacetal.

It is particularly preferred in the aforementioned methods if the protective groups on the H in $R^{01}$, $R^{02}$, $R^{04}$ and/or $R^{05}$ are alkyl, benzyl or carbamates, for example, or fluorenyl-methyl-chloroformate (FMOC) groups, benzyloxycarbonyl (Z) groups or tert-butyloxycarbonyl (Boc) groups.

Certain embodiments of the invention are explained further by the following examples, which are provided for purposes of explanation and illustration only and are not intended to, and should not be deemed to, limit the scope of the claims appended hereto.

EXAMPLES

The following examples show compounds according to certain embodiments of the invention and the preparation thereof and efficacy tests carried out therewith.

In general the following details apply:

The chemicals and solvents used were acquired commercially from conventional suppliers (Acros, Avocado, Aldrich, Fluka, Lancaster, Maybridge, Merck, Sigma, TCI etc.) or synthesized.

Analyses were made by NMR spectroscopy, optionally combined with other methods of analysis such as thin-layer chromatography, mass spectrometry or HPLC.

Example 1

General Method of Producing Compounds According to the Invention

The compounds are produced, starting from a cyclohexane-1,4-dione corresponding to formula II suitably protected as, for example, monoacetal. A protected N-substituted 1-amino-4-oxo-cyclohexane carbonitrile compound corresponding to formula III is obtained by reaction with potassium cyanide in the presence of a secondary amine.

The reaction of the aminonitrile corresponding to formula III with organometallic reagents, preferably Grignard or organolithium reagents, results in substitution of the nitrile function, so a 4-substituted 4-aminocyclohexanone compound corresponding to formula IV is obtained after subsequently removing the carbonyl protective group.

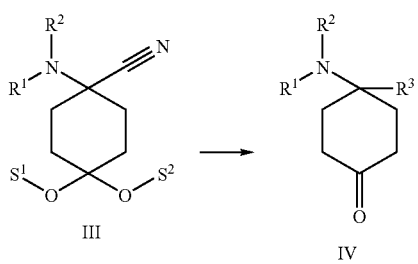

Intermediates corresponding to formula IV may finally be converted into 4-aminocyclohexanols corresponding to formula I according to the invention by addition of organometallic reagents, preferably Grignard organolithium reagents.

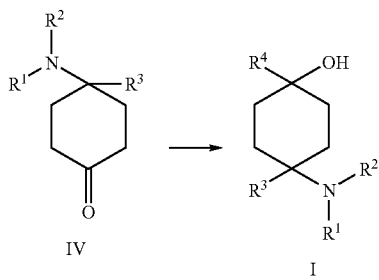

Example 2

Measurement of the ORL1 Bond

The 4-aminocyclohexanols corresponding to formula I were investigated in a receptor binding assay with $^3$H-nociceptin/Orphanin FQ with membranes of recombinant CHO—ORL1 cells. This test system was carried out by the method presented by Ardati et al. (Mol. Pharmacol., 51, 1997, pp. 816–824). The concentration of $^3$H-nociceptin/Orphanin FQ was 0.5 nM in these tests.

The binding assays were carried out with 20 μg membrane protein per 200 μl mixture in 50 mM Hepes, pH 7.4, 10 mM $MgCl_2$ and 1 mM EDTA respectively. Binding to the ORL1 receptor was determined using 1 mg WGA-SPA beads (Amersham-Pharmacia, Freiburg), respectively, by incubation of the mixture for one hour at ambient temperature and subsequent measurement in the Trilux scintillation counter (Wallac, Finland). The affinity is indicated as the $K_i$ value.

The affinity to the ORL1 receptor was determined according to the specified molecular-pharmacological investigations in each of the following examples 4 to 12. The corresponding $K_i$ values are given in the following table 1.

TABLE 1

ORL1 binding assay data

| Example | Ki (nM) |
|---------|---------|
| 4 | 4.4 |
| 5 | 10 |
| 6 | 9.0 |
| 7 | 24 |
| 8 | 7.2 |
| 9 | 3.4 |

TABLE 1-continued

ORL1 binding assay data

| Example | Ki (nM) |
|---------|---------|
| 10 | 110 |
| 11 | 66 |
| 12 | 430 |

Example 3

Analgesia Test by the Tail-flick Test on Mice

The analgesic effectiveness of the compounds according to the invention was investigated in the focal ray (tail-flick) test on mice by D'Amour and Smith's method (J. Pharm. Exp. Ther. 72, 74 79 (1941)). NMRI mice weighing between 20 and 24 g were used for this purpose. The animals were placed individually in specific test cages and the tail base was exposed to a focused ray of heat from an electric lamp (Tail-flick Typ 55/12/10.fl, Labtec, Dr. Hess). The intensity of the lamp was adjusted such that the time from the switching on of the lamp to the sudden jerking away of the tail (latency of pain) was 3 to 5 seconds in untreated animals. Prior to administration of a compound according to the invention, the animals were pre-tested twice within five minutes and the average value of these measurements was calculated as the pre-test average. The pain was measured 20, 40 and 60 min after intravenous administration. The analgesic effect was determined as an increase in the latency of pain (% MPE) by the following formula:

$$[(T_1-T_0)/(T_2-T_0)] \times 100.$$

To is the latency time before application of the substance, $T_1$ the latency time after application and $T_2$ the maximum exposure time (12 sec).

To determine the dose dependency, the respective compound according to the invention was applied in 3 to 5 logarithmically increasing doses, which each concluded the threshold and the maximum active dose, and the $ED_{50}$ values were determined by regression analysis. The $ED_{50}$ was calculated at the peak of action 20 minutes after intravenous administration of the substance.

The investigated compounds according to the invention exhibited a pronounced analgesic effect. The results are compiled in the following table.

| Example No. | % MPE (intravenous dosage in mg/kg) | $ED_{50}$ intravenous mg/kg |
|-------------|--------------------------------------|------------------------------|
| 4 | 100 (0.1) | 0.009 |
| 5 | 35 (0.001) | 0.01–0.001 |
|   | 79 (0.01) |   |
| 6 | 43 (0.001) | 0.001 |
|   | 96 (0.01) |   |
| 7 | 100 (1) | 0.19 |
| 9 | 100 (1) |   |

Example 4

4-dimethylamino-1-phenethyl-4-phenylcyclohexanol

Starting with 200 g 1,4-dioxaspiro[4.5]decan-8-one, 168 l aqueous dimethylamine solution (40% by volume), 200 ml methanol, 200 g potassium cyanide and 303 g dimethylamine hydrochloride were added and the reaction mixture was stirred for 65 hours at ambient temperature. The resultant white suspension was extracted four times with 800 ml diethylether in each case, the combined extracts were initially concentrated and taken up with 500 ml dichloromethane, the organic phase was separated, dried over sodium sulfate, filtered, concentrated and substantially freed of solvent residues under vacuum. 265 g 8-dimethylamino-1,4-dioxaspiro[4.5]decane-8-carbonitrile were obtained as a white solid.

30 g 8-dimethylamino-1,4-dioxaspiro[4.5] decane-8-carbonitrile were dissolved in 300 ml tetrahydrofuran, 143 ml 2.0 molar phenyl magnesium chloride solution in THF were added under a nitrogen atmosphere and stirred overnight at ambient temperature. To work up the mixture, 100 ml ammonium chloride solution (20% by weight) were added with ice cooling, the phases were separated, the aqueous phase was extracted twice with 250 ml diethylether in each case, the combined organic phases were dried over sodium sulfate, filtered, concentrated and substantially freed from solvent residues under vacuum. The crude dimethyl-(8-phenyl-1,4-dioxaspiro[4.5]dec-8-yl)amine (34.5 g) obtained was stirred for 48 hours with a mixture of 83 ml concentrated hydrochloric acid (32% by weight) and 48 ml water at ambient temperature without further purification. Subsequently the reaction mixture was first washed three times with 50 ml diethylether in each case, then alkalized by addition of 100 ml sodium hydroxide solution (32% by weight) with ice cooling, extracted three times with 100 ml dichloromethane in each case, the combined dichloromethane extracts were dried over sodium sulfate, filtered, concentrated and substantially freed of solvent residues under vacuum. 18.8 g 4-dimethylamino-4-phenylcyclohexanone were obtained.

3.83 g 4-dimethylamino-4-phenylcyclohexanone dissolved in 10 ml tetrahydrofuran were added dropwise to 21 ml 1.0 molar phenethyl magnesium chloride solution in tetrahydrofuran and the mixture was stirred overnight at ambient temperature. To work up the mixture with ice cooling, 15 ml ammonium chloride solution (20% by weight) were added, the mixture was extracted three times with 15 ml ethylacetate in each case, the extracts were combined, dried over sodium sulfate, filtered, concentrated and substantially freed of solvent residues under vacuum. The crude 4-dimethylamino-1-phenethyl-4-phenylcyclohexanol (5.75 g) obtained was obtained as a brown oil which was chromatographed with diethylether/hexane (V:V=1:1) over silica gel. 1.71 g 4-dimethylamino-1-phenethyl-4-phenylcohexanol were obtained in the form of yellow crystals which were dissolved in 6.8 ml 2-butanone and converted by reaction with 26 μl water and 366 μl chlorotrimethylsilane, stirring overnight with subsequent filtration into 838 mg of the corresponding hydrochloride.

Example 5

4-(4-chlorophenyl)-4-dimethylamino-1-phenethylcyclohexanol

Starting with 38 ml 1.0 molar 4-chlorophenyl magnesium chloride solution in diethylether, 4.00 g 8-dimethylamino-1,4-dioxaspiro[4.5]decane-8-carbonitrile, dissolved in 60 ml diethylether, were added dropwise and stirred overnight at ambient temperature. To work up the mixture, 30 ml ammonium chloride solution (20% by weight) were added with ice cooling, the phases were separated, the ethereal phase was washed in succession with 30 ml water and saturated sodium chloride solution, dried over sodium sulfate, filtered, concentrated and substantially freed of solvent residues under vacuum. The crude [-(4-chlorophenyl)-1,4-dioxaspiro[4.5] dec-8-yl]dimethylamine (4.18 g) obtained was initially stirred for 24 hours with a mixture of 10 ml concentrated hydrochloric acid (32% by weight) and 6.0 ml water at ambient temperature without further purification and then heated for 3 hours to reflux. Subsequently, the reaction mixture was first washed three times with 50 ml diethylether in each case, then made basic by addition of concentrated ammonia solution (25% by weight) with ice cooling, extracted three times with 100 ml diethylether in each case, the combined diethylether extracts were dried over sodium sulfate, filtered, concentrated and substantially freed of solvent residues under vacuum. 3.84 g 4-(4-chlorophenyl)-4-dimethylaminocyclohexanone were obtained as a brown oil.

3.50 g 4-(4-chlorophenyl)-4-dimethylaminocyclohexanone dissolved in 20 ml tetrahydrofuran were added dropwise to 17 ml 1.0 molar phenethyl magnesium chloride solution in tetrahydrofuran and the mixture was stirred overnight at ambient temperature. To work up the mixture, 25 ml ammonium chloride solution (20% by weight) were added with ice cooling, the phases were separated, the mixture was extracted three times with 25 ml diethylether in each case, the combined organic phases were dried over sodium sulfate, filtered, concentrated and substantially freed of solvent residues under vacuum. The crude product obtained (4.54 g) was taken up in 50 ml diethylether, extracted three times with 40 ml hydrochloric acid (5% by weight) in each case and the combined extracts were washed twice with 40 ml dichloromethane in each case. The dichloromethane extracts were dried over sodium sulfate, filtered, concentrated and substantially freed of solvent residues under vacuum. 1.77 g of a yellow resin were obtained and chromatographed with diethylether/hexane (V:V=2:1) over silica gel. The 417 mg 4-(4-chlorophenyl)-4-dimethylamino-1-phenethylcyclohexanol obtained were dissolved in 4.8 ml 2-butanone and converted by reaction with 162 μl chlorotrimethylsilane and 12 μl water, stirring overnight with subsequent filtration, diethylether washing and vacuum drying into 416 mg of the corresponding hydrochloride.

Example 6

4-(4-bromophenyl)-4-dimethylamino-1-phenethylcyclohexanol 26.6 g 4-bromoiodobenzene were placed in 150 ml diethylether and 47 ml 2.0 molar isopropyl magnesium chloride solution were added dropwise at ambient temperature. After one further hour, 18 g 8-dimethylamino-1,4-dioxaspiro[4.5] decane-8-carbonitrile, dissolved in 250 ml diethylether, were added dropwise and stirred overnight. To work up the mixture with ice cooling, 20 ml ammonium chloride solution (20% by weight) were added, extracted three times with 100 ml diethylether in each case, the combined organic phases were dried over sodium sulfate, filtered, concentrated and substantially freed of solvent residues under vacuum. The crude product (21.8 g) obtained was chromatographed with diethylether over silica gel. 7.49 g 4-(4-bromophenyl)-4-dimethylamino-1-phenethylcyclohexanol were obtained as a colorless liquid.

7.48 g 4-(4-bromophenyl)-4-dimethylamino-1-phenethyl-cyclohexanol were dissolved in 30 ml diisopropylether and 10 ml diethylether and were stirred for 4 days with 13 ml 4-molar hydrochloric acid. To work up the reaction mixture, it was alkalized by addition of sodium hydroxide solution (32% by weight), extracted three times with 30 ml dichloromethane in each case, the combined extracts were dried over sodium sulfate, filtered, concentrated and substantially freed of solvent residues under vacuum. The 5.02 g 4-(4-bromophenyl)-4-dimethylaminocyclohexanone obtained, dissolved in 22 ml tetrahydrofuran, were added dropwise to 18 ml 1.0 molar phenethyl magnesium chloride solution in THF in a nitrogen atmosphere at ambient temperature and were stirred overnight. To work up the mixture with ice cooling, 28 ml ammonium chloride solution (20% by weight) were added, the phases were separated, the mixture was extracted three times with 25 ml diethylether in each case, the combined organic phases were dried over sodium sulfate, filtered, concentrated and substantially freed of solvent residues under vacuum. The crude product obtained (5.83 g) was taken up in 50 ml diethylether, extracted three times with 40 ml hydrochloric acid (5% by weight) in each case and the combined extracts were washed twice with 40 ml dichloromethane in each case. The dichloromethane extracts were dried over sodium sulfate, filtered, concentrated and substantially freed of solvent residues under vacuum. 3.66 g of a light brown resin were obtained and were chromatographed with diethylether/hexane (V:V=2:1) over silica gel. The 1.38 g 4-(4-bromophenyl)-4-dimethylaminocyclohexanone obtained were dissolved in 20 ml 2-butanone and converted by reaction with 474 µl chlorotrimethylsilane and 34 µl water, stirring overnight with subsequent filtration, diethylether washing and vacuum drying, into 1.47 mg of the corresponding hydrochloride.

Example 7

4-dimethylamino-1-(1-methyl-1H-indol-2-yl)-4-phenylcyclohexanol

A solution of N-methylindol (400 mg, 3.05 mmol) in dry THF (20 ml) was cooled to −5° C. under a stream of argon. Tert-butyllithium (3.65 mmol, 2.15 ml of a 1.7 molar pentane solution) was added dropwise in such a way that a reaction temperature of 0° C. was not exceeded. Once all the substance had been added, the reaction mixture was stirred for 2 hours at 0° C. A solution of 4-dimethylamino-4-phenylcyclohexanone (662 mg, 3.05 mmol) in dry THF (5 ml) was added dropwise at 0° C. The mixture was stirred for 15 minutes at 0° C. and then 4 hours at ambient temperature. The reaction mixture was quenched with saturated ammonium chloride solution (20 ml), the organic phase was separated and the aqueous phase extracted four times with dichloromethane (20 ml). The combined organic phases were dried over sodium sulfate, filtered and the solvent removed under vacuum. Purification was carried out by flash chromatography with cyclohexane/ethylacetate (V:V=7:3) over silica gel. 318 mg 4-dimethylamino-1-(1-methyl-1H-indol-2-yl)-4-phenylcyclohexanol with a melting point of 163–165° C. were obtained.

Example 8

1-benzo[b]thiophen-2-yl-4-dimethylamino-4-phenylcyclohexanol

A solution of benzo[b]thiophene (400 mg, 2.98 mmol) in dry THF (20 ml) was cooled to −5° C. under a stream of argon. Tert-butyllithium (3.58 mmol, 2.11 ml of a 1.7 molar pentane solution) was carefully added dropwise, to avoid exceeding a reaction temperature of 0° C. Once all the substance had been added, the reaction mixture was stirred for 2 hours at 0° C. A solution of 4-dimethylamino-4-phenylcyclohexanone (648 mg, 2.98 mmol) in dry THF (5 ml) was then added dropwise at 0° C. The mixture was stirred for 15 minutes at 0° C. and then 6 hours at ambient temperature. The reaction mixture was quenched with saturated ammonium chloride solution (20 ml), the organic phase was separated and the aqueous phase extracted four times with dichloromethane (20 ml). The combined organic phases were dried over sodium sulfate, filtered and the solvent was removed under vacuum. Purification was carried out by flash chromatography over silica gel with cyclohexane/ethylacetate (V:V=1:1). 345 mg 1-benzo[b]thiophen-2-yl-4-dimethylamino-4-phenylcyclohexanol with a melting point of 183–185° C. were obtained.

Example 9

1-benzo[b]thiophen-3-yl-4-dimethylamino-4-phenylcyclohexanol

A solution of 3-bromo-1-benzo[b]thiophene (1.00 g, 4.69 mmol) in 30 ml dry tetrahydrofuran was cooled to −78° C. under a stream of argon. n-butyllithium (5.63 mmol, 3.52 ml of a 15% by weight hexane solution) were added dropwise in such a way that a reaction temperature of −75° C. was not exceeded. Once all the substance had been added, the reaction mixture was stirred for 2 hours at 78° C. A solution of 4-dimethylamino-4-phenylcyclohexanone (1.02 g, 4.69 mmol) in dry THF (15 ml) was added dropwise at 78° C. The reaction mixture was stirred for 2 hours at −78° C. and then thawed within about 10 hours at ambient temperature. The reaction mixture was quenched with saturated ammonium chloride solution (30 ml), the organic phase was separated and the aqueous phase extracted four times with dichloromethane (25 ml). The combined organic phases were dried over sodium sulfate, filtered and the solvent removed under vacuum. Purification was carried out by flash chromatography with cyclohexane/ethylacetate (V:V=7:3) over silica gel. 445 mg 1-benzo[b]thiophen-3-yl-4-dimethylamino-4-phenylcyclohexanol with a melting point of 176–178° C. were obtained.

Example 10

1-(1-benzenesulfonyl-1H-indol-2-yl)-4-dimethylamino-4-phenylcyclohexanol

A solution of 1-benzenesulfonyl-1H-indol (600 mg, 2.33 mmol) in dry THF (30 ml) was cooled to −5° C. under a stream of argon. n-butyllithium (2.79 mmol, 1.75 ml of a 1.6 molar hexane solution) were added dropwise in such a way that a reaction temperature of 0° C. was not exceeded. Once all the substance had been added, the reaction mixture was stirred for 2 hours at 0° C. A solution of 4-dimethylamino-4-phenylcyclohexanone (493 mg, 2.33 mmol) in dry THF (5 ml) was added dropwise at 0° C. The mixture was stirred for 1 hour at 0° C. and then 3 days at ambient temperature. The reaction mixture was quenched with saturated ammonium chloride solution (20 ml), the organic phase was separated and the aqueous phase extracted four times with dichloromethane (20 ml). The combined organic phases were dried over sodium sulfate, filtered and the solvent removed under vacuum. Purification was carried out by flash chromatography with cyclohexane/ethylacetate (V:V=1:1) over silica gel. 232 mg 1-(1-benzenesulfonyl-1H-indol-2-yl)-4-dimethylamino-4-phenylcyclohexanol with a melting point of 173–176° C. were obtained.

Example 11

1-benzofuran-2-yl-4-dimethylamino-4-phenylcyclohexanol

A solution of benzo[b]furan (1.50 g, 12.7 mmol) in dry THF (50 ml) was cooled to −8° C. under a stream of argon.

Tert-butyllithium (15.2 mmol, 10.2 ml of a 1.5 molar pentane solution) was added dropwise in such a way that a reaction temperature of −5° C. was not exceeded. Once all the substance had been added, the reaction mixture was stirred for 2½ hours at −5° C. A solution of 4-dimethylamino-4-phenylcyclohexanone (2.76 g, 12.7 mmol) in dry THF (15 ml) was added dropwise at 0° C. The mixture was stirred for 1 hour at 0° C. and then 4 days at ambient temperature. The reaction mixture was quenched with saturated ammonium chloride solution (30 ml), the organic phase was separated and the aqueous phase extracted four times with dichloromethane (30 ml). The combined organic phases were dried over sodium sulfate, filtered and the solvent removed under vacuum. Purification was carried out by flash chromatography with cyclohexane/ethylacetate (V:V=7:3) over silica gel. 1.02 g 1-benzofuran-2-yl-4-dimethylamino-4-phenylcyclohexanol with a melting point of 134–137° C. were obtained.

Example 12

1-benzothiazol-2-yl-4-dimethylamino-4-phenylcyclohexanol

A solution of benzothiazole (622 mg, 4.60 mmol) in dry THF (30 ml) was cooled to −85° C. under a stream of argon. n-butyllithium (5.52 mmol, 3.45 ml of a 1.6 molar hexane solution) was added dropwise in such a way that a reaction temperature of −78° C. was not exceeded. Once all the substance had been added, the reaction mixture was stirred for 2 hours at −80° C. A solution of 4-dimethylamino-4-phenylcyclohexanone (1.00 g, 4.61 mmol) in dry THF (8 ml) was added dropwise at −80° C. The mixture was stirred for 30 minutes at −80° C. and then 3 days at ambient temperature. The reaction mixture was quenched with saturated ammonium chloride solution (30 ml), the organic phase was separated and the aqueous phase extracted four times with dichloromethane (30 ml). The combined organic phases were dried over sodium sulfate, filtered and the solvent removed under vacuum. Purification was carried out b y flash chromatography with cyclohexane/ethylacetate (V:V=7:3) over silica gel. 746 mg 1-benzothiazol-2-yl-4-dimethylamino-4-phenylcyclohexanol with a melting point of 155–157° C. were obtained.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted 4-aminocyclohexanol compound corresponding to formula I,

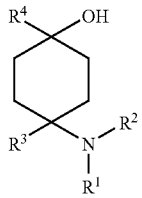

I wherein $R^1$ and $R^2$ independently of one another represent H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl; wherein $R^1$ and $R^2$ are not both H, or the radicals $R^1$ and $R^2$ together form a ring and represent $CH_2CH_2OCH_2CH_2$, $CH_2CH_2NR^5CH_2CH_2$ or $(CH_2)_{3-6}$, wherein $R^5$ represents H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl;

$R^3$ represents unsubstituted or singly or multiply substituted aryl or heteroaryl;

$R^4$ represents unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$ wherein $Y=O$, S or $H_2$;

$R^6$ represents H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;

$R^7$ represents H; unsubstituted or singly or multiply substituted $C_{3-8}$-cycloalkyl, aryl or heteroaryl;

$R^8$ represents unsubstituted or singly or multiply substituted aryl or heteroaryl;

L represents —C(O)—NH—, —NH—C(O)—, —C(O)—O—, —O—C(O)—, —O—, —S— or —$S(O)_2$—; and $R^9$ represents unsubstituted or singly or multiply substituted aryl or heteroaryl, or an acid, base, solvate or a physiologically acceptable salt thereof provided that, if $R^3$=substituted or unsubstituted phenyl, and $R^4$=phenyl or —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$ where $Y=H_2$, $R^6$=H, saturated or unsaturated, branched or unbranched, singly or multiply substituted or unsubstituted $C_{1-5}$-alkyl, or $R^7$=H, substituted or unsubstituted $C_{3-8}$-cycloalkyl or phenyl, then $R^1$ and $R^2$ independently of one another are not both $C_{1-5}$-alkyl, or if $R^3$=substituted or unsubstituted thiophenyl, and $R^4$=—$CH_2$—$CH_2$-phenyl, then the radicals $R^1$ and $R^2$ do not together form a ring and represent $(CH_2)_5$.

2. A substituted 4-aminocyclohexanol compound corresponding to formula I of claim 1,

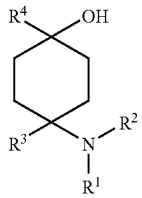

wherein
the radicals $R^1$ and $R^2$ together form a ring and represent $CH_2CH_2OCH_2CH_2$, $CH_2CH_2NR^5CH_2CH_2$ or $(CH_2)_{3-6}$,
where $R^5$ represents H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl;

$R^3$ represents unsubstituted or singly or multiply substituted aryl or heteroaryl;

$R^4$ represents unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$
wherein
Y=O, S or $H_2$;
$R^6$ represents H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
$R^7$ represents H; unsubstituted or singly or multiply substituted $C_{3-8}$-cycloalkyl, aryl or heteroaryl;
$R^8$ represents unsubstituted or singly or multiply substituted aryl or heteroaryl;
L represents —C(O)—NH—, —NH—C(O)—, —C(O)—O—, —O—C(O)—, —O—, —S— or —S(O)$_2$—; and
$R^9$ represents unsubstituted or singly or multiply substituted aryl or heteroaryl,
provided that,
if $R^3$=substituted or unsubstituted thiophenyl, and $R^4$=—$CH_2$—$CH_2$-phenyl, the radicals $R^1$ and $R^2$ do not together form a ring and represent $(CH_2)_5$, or a salt thereof with a physiologically tolerated acid.

3. A substituted 4-aminocyclohexanol compound corresponding to formula I of claim 1,

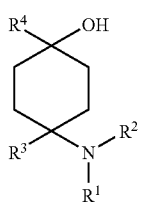

wherein
$R^1$ and $R^2$ independently of one another represent H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl; wherein $R^1$ and $R^2$ are not both H, $R^3$ represents unsubstituted or singly or multiply substituted aryl or heteroaryl;

$R^4$ represents unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$
wherein
Y=O, S or $H_2$;
$R^6$ represents H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
$R^7$ represents H; unsubstituted or singly or multiply substituted $C_{3-8}$-cycloalkyl, aryl or heteroaryl;
$R^8$ represents unsubstituted or singly or multiply substituted aryl or heteroaryl;
L represents —C(O)—NH—, —NH—C(O)—, —C(O)—O—, —O—C(O)—, —O—, —S— or —S(O)$_2$—; and
$R^9$ represents unsubstituted or singly or multiply substituted aryl or heteroaryl,
or an acid, base, solvate or a physiologically acceptable salt thereof
provided that,
if $R^3$=substituted or unsubstituted phenyl, and $R^4$=phenyl or —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$
where Y=$H_2$,
$R^6$=H, saturated or unsaturated, branched or unbranched, singly or multiply substituted or unsubstituted $C_{1-5}$-alkyl, or
$R^7$=H, substituted or unsubstituted $C_{3-8}$-cycloalkyl or phenyl, then
$R^1$ and $R^2$ independently of one another are not both $C_{1-5}$-alkyl,
or
if $R^3$=substituted or unsubstituted thiophenyl, and $R^4$=—$CH_2$—$CH_2$-phenyl, then
the radicals $R^1$ and $R^2$ do not together form a ring and represent $(CH_2)_5$.

4. A substituted 4-aminocyclohexanol corresponding to formula I of claim 1,

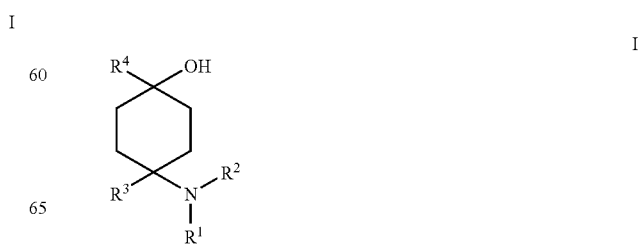

wherein
R$^1$ and R$^2$ independently of one another represent H; saturated or unsaturated, branched or unbranched, singly or multiply substituted or unsubstituted C$_{1-8}$-alkyl or C$_{3-8}$-cycloalkyl; singly or multiply substituted or unsubstituted aryl or heteroaryl; or singly or multiply substituted or unsubstituted aryl bound via C$_{1-3}$-alkylene, C$_{3-8}$-cycloalkyl or heteroaryl; wherein R$^1$ and R$^2$ are not both H, or the radicals R$^1$ and R$^2$ together form a ring and represent CH$_2$CH$_2$OCH$_2$CH$_2$, CH$_2$CH$_2$NR$^5$CH$_2$CH$_2$ or (CH$_2$)$_{3-6}$,
wherein R$^5$ represents H; saturated or unsaturated, branched or unbranched, singly or multiply substituted or unsubstituted C$_{1-8}$-alkyl or C$_{3-8}$-cycloalkyl; singly or multiply substituted or unsubstituted aryl or heteroaryl; or singly or multiply substituted or unsubstituted aryl bound via C$_{1-3}$-alkylene, C$_{3-8}$-cycloalkyl or heteroaryl;

R$^3$ represents unsubstituted or singly or multiply substituted heteroaryl;

R$^4$ represents unsubstituted or singly or multiply substituted C$_{3-8}$-cycloalkyl, aryl or heteroaryl; —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$; or —R$^8$-L-R$^9$ wherein
Y=O, S or H$_2$;

R$^6$ represents H, saturated or unsaturated, branched or unbranched, singly or multiply substituted or unsubstituted C$_{1-7}$-alkyl; or saturated or unsaturated, branched or unbranched, singly or multiply substituted or unsubstituted C(O)O—C$_{1-6}$-alkyl;

R$^7$ represents H; unsubstituted or singly or multiply substituted C$_{3-8}$-cycloalkyl, aryl or heteroaryl;

R$^8$ represents unsubstituted or singly or multiply substituted aryl or heteroaryl;

L represents —C(O)—NH—, —NH—C(O)—, —C(O)—O—, —O—C(O)—, —O—, —S— or —S(O)$_2$—; and R$^9$ represents unsubstituted or singly or multiply substituted aryl or heteroaryl;

provided that,
if R$^3$=substituted or unsubstituted thiophenyl, and R$^4$=—CH$_2$—CH$_2$-phenyl, the radicals R$^1$ and R$^2$ do not together form a ring and represent (CH$_2$)$_5$, or a salt thereof with a physiologically tolerated acid.

5. A substituted 4-aminocyclohexanol compound corresponding to formula I of claim 1,

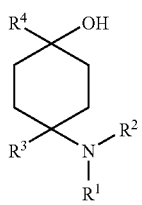

I wherein
R$^1$ and R$^2$ independently of one another represent H; saturated or unsaturated, branched or unbranched, singly or multiply substituted or unsubstituted C$_{1-8}$-alkyl or C$_{3-8}$-cycloalkyl; singly or multiply substituted or unsubstituted aryl or heteroaryl; or singly or multiply substituted or unsubstituted aryl bound via C$_{1-3}$-alkylene, C$_{3-8}$-cycloalkyl or heteroaryl; wherein R$^1$ and R$^2$ are not both H, or the radicals R$^1$ and R$^2$ together form a ring and represent CH$_2$CH$_2$OCH$_2$CH$_2$, CH$_2$CH$_2$NR$^5$CH$_2$CH$_2$ or (CH$_2$)$_{3-6}$,
wherein R$^5$ represents H; saturated or unsaturated, branched or unbranched, singly or multiply substituted or unsubstituted C$_{1-8}$-alkyl or C$_{3-8}$-cycloalkyl; singly or multiply substituted or unsubstituted aryl or heteroaryl; or singly or multiply substituted or unsubstituted aryl bound via C$_{1-3}$-alkylene, C$_{3-8}$-cycloalkyl or heteroaryl;

R$^3$ represents unsubstituted or singly or multiply substituted aryl;

R$^4$ represents unsubstituted or singly or multiply substituted C$_{3-8}$-cycloalkyl, aryl or heteroaryl; —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$; or —R$^8$-L-R$^9$ wherein
Y=O, S or H$_2$;

R$^6$ represents H, saturated or unsaturated, branched or unbranched, singly or multiply substituted or unsubstituted C$_{1-7}$-alkyl; or saturated or unsaturated, branched or unbranched, singly or multiply substituted or unsubstituted C(O)O—C$_{1-6}$-alkyl;

R$^7$ represents H; unsubstituted or singly or multiply substituted C$_{3-8}$-cycloalkyl, aryl or heteroaryl;

R$^8$ represents unsubstituted or singly or multiply substituted aryl or heteroaryl;

L represents —C(O)—NH—, —NH—C(O)—, —C(O)—O—, —O—C(O)—, —O—, —S— or —S(O)$_2$—; and R$^9$ represents unsubstituted or singly or multiply substituted aryl or heteroaryl, or an acid, base, solvate or a physiologically acceptable salt thereof provided that,
if R$^3$=substituted or unsubstituted phenyl, and R$^4$=phenyl or —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ where Y=H$_2$,
R$^6$=H, saturated or unsaturated, branched or unbranched, singly or multiply substituted or unsubstituted C$_{1-5}$-alkyl, or R$^7$=H, substituted or unsubstituted C$_{3-8}$-cycloalkyl or phenyl, then R$^1$ and R$^2$ independently of one another are not both C$_{1-5}$-alkyl, or
if R$^3$=substituted or unsubstituted thiophenyl, and R$^4$=—CH$_2$—CH$_2$-phenyl, then the radicals R$^1$ and R$^2$ do not together form a ring and represent (CH$_2$)$_5$.

6. A substituted 4-aminocyclohexanol compound corresponding to formula I of claim 1,

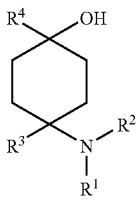

wherein
the radicals $R^1$ and $R^2$ together form a ring and represent $CH_2CH_2OCH_2CH_2$, $CH_2CH_2NR^5CH_2CH_2$ or $(CH_2)_{3-6}$,
wherein $R^5$ represents H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl;
$R^3$ represents unsubstituted or singly or multiply substituted aryl;
$R^4$ represents unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$
wherein
Y=O, S or $H_2$;
$R^6$ represents H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
$R^7$ represents H; unsubstituted or singly or multiply substituted $C_{3-8}$-cycloalkyl, aryl or heteroaryl;
$R^8$ represents unsubstituted or singly or multiply substituted aryl or heteroaryl;
L represents —C(O)—NH—, —NH—C(O)—, —C(O)—O—, —O—C(O)—, —O—, —S— or —S(O)$_2$—; and
$R^9$ unsubstituted or singly or multiply substituted aryl or heteroaryl,
or a salt thereof with a physiologically tolerated acid.

7. A substituted 4-aminocyclohexanol compound corresponding to formula I of claim 1,

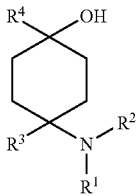

wherein
$R^1$ and $R^2$ independently of one another represent H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl; wherein $R^1$ and $R^2$ are not both H,
$R^3$ represents unsubstituted or singly or multiply substituted heteroaryl;
$R^4$ represents unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$
wherein
Y=O, S or $H_2$;
$R^6$ represents H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
$R^7$ represents H; unsubstituted or singly or multiply substituted $C_{3-8}$-cycloalkyl, aryl or heteroaryl;
$R^8$ represents unsubstituted or singly or multiply substituted aryl or heteroaryl;
L represents —C(O)—NH—, —NH—C(O)—, —C(O)—O—, —O—C(O)—, —O—, —S— or —S(O)$_2$—; and
$R^9$ represents unsubstituted or singly or multiply substituted aryl or heteroaryl,
or a salt thereof with a physiologically tolerated acid.

8. A substituted 4-aminocyclohexanol compound corresponding to formula I of claim 1,

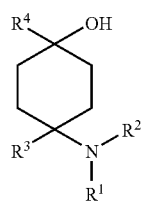

wherein
$R^1$ and $R^2$ independently of one another represent H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl; wherein $R^1$ and $R^2$ are not both H, or the radicals $R^1$ and $R^2$ together form a ring and represent $CH_2CH_2OCH_2CH_2$, $CH_2CH_2NR^5CH_2CH_2$ or $(CH_2)_{3-6}$,
wherein $R^5$ represents H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl;
$R^3$ represents unsubstituted or singly or multiply substituted aryl or heteroaryl;
$R^4$ represents unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—

$CH_2R^7$, —C(Y)—$CH_2$—$CH_2R^7$ or —C(Y)—$CH_2$—$CH_2$—$CH_2R^7$; or —$R^8$-L-$R^9$ wherein

Y=$H_2$, $R^6$ represents H, saturated or unsaturated, branched or unbranched, singly or multiply substituted or unsubstituted $C_{1-7}$-alkyl $R^7$ represents unsubstituted or singly or multiply substituted heteroaryl, $R^8$ represents unsubstituted or singly or multiply substituted aryl or heteroaryl, L represents —C(O)—NH—, —NH—C(O)—, —C(O)—O—, —O—C(O)—, —O—, —S— or —S(O)$_2$—; and $R^9$ represents unsubstituted or singly or multiply substituted aryl or heteroaryl, or a salt thereof with a physiologically tolerated acid.

9. A substituted 4-aminocyclohexanol compound corresponding to formula I of claim 1,

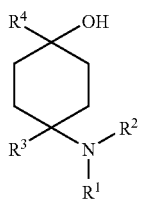

I wherein $R^1$ and $R^2$ independently of one another represent H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl; wherein $R^1$ and $R^2$ are not both H, or the radicals $R^1$ and $R^2$ together form a ring and represent $CH_2CH_2OCH_2CH_2$, $CH_2CH_2NR^5CH_2CH_2$ or $(CH_2)_{3-6}$;

wherein $R^5$ represents H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl;

$R^3$ represents unsubstituted or singly or multiply substituted aryl or heteroaryl;

$R^4$ represents —$CHR^6R^7$, —$CHR^6$—$CH_2R^7$, —$CHR^6$—$CH_2$—$CH_2R^7$ or —$CHR^6$—$CH_2$—$CH_2R^7$;

$R^6$ represents saturated or unsaturated, branched or unbranched, singly or multiply substituted or unsubstituted C(O)O—$C_{1-6}$-alkyl; and $R^7$ represents H; respectively unsubstituted or singly or multiply substituted $C_{3-8}$-cycloalkyl, aryl or heteroaryl, or a salt thereof with a physiologically tolerated acid.

10. A substituted 4-aminocyclohexanol compound corresponding to formula I of claim 1,

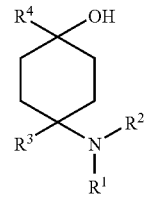

I wherein $R^1$ and $R^2$ independently of one another represent H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl; wherein $R^1$ and $R^2$ are not both H, or the radicals $R^1$ and $R^2$ together form a ring and represent $CH_2CH_2OCH_2CH_2$, $CH_2CH_2NR^5CH_2CH_2$ or $(CH_2)_{3-6}$, wherein $R^5$ represents H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl;

$R^3$ represents unsubstituted or singly or multiply substituted aryl or heteroaryl;

$R^4$ represents —$C(Y)R^7$, —C(Y)—$CH_2R^7$, —C(Y)—$CH_2$—$CH_2R^7$ or —C(Y)—$CH_2$—$CH_2$—$CH_2R^7$;

wherein

Y=O or S; and $R^7$ represents H; unsubstituted or singly or multiply substituted $C_{3-8}$-cycloalkyl, aryl or heteroaryl, or a salt thereof with a physiologically tolerated acid.

11. A substituted 4-aminocyclohexanol compound according to claim 1 wherein:

$R^1$ and $R^2$ independently of one another represent H; saturated or unsaturated, branched or unbranched, singly or multiply substituted or unsubstituted $C_{1-8}$-alkyl; wherein $R^1$ and $R^2$ are not both H, or the radicals $R^1$ and $R^2$ together form a ring and represent $CH_2CH_2OCH_2CH_2$, $CH_2CH_2NR^5CH_2CH_2$ or $(CH_2)_{3-6}$, where $R^5$ represents H; saturated or unsaturated, branched or unbranched, singly or multiply substituted or unsubstituted $C_{1-8}$-alkyl.

12. A substituted 4-aminocyclohexanol compound according to claim 3, wherein $R^1$ and $R^2$ independently of one another represent H; saturated or unsaturated, branched or unbranched, singly or multiply substituted or unsubstituted $C_{1-8}$-alkyl; wherein $R^1$ and $R^2$ are not both H.

13. A substituted 4-aminocyclohexanol compound according to claim 7, wherein $R^1$ and $R^2$ independently of one another represent H; saturated or unsaturated, branched or unbranched, singly or multiply substituted or unsubstituted $C_{1-8}$-alkyl; wherein $R^1$ and $R^2$ are not both H.

14. A substituted 4-aminocyclohexanol compound according to claim 2, wherein $R^1$ and $R^2$ together form a ring and represent $CH_2CH_2OCH_2CH_2$, $CH_2CH_2NR^5CH_2CH_2$ or $(CH_2)_{3-6}$,
wherein $R^5$ represents H; saturated or unsaturated, branched or unbranched, singly or multiply substituted or unsubstituted $C_{1-8}$-alkyl.

15. A substituted 4-aminocyclohexanol compound according to claim 6, wherein
$R^1$ and $R^2$ together form a ring and represent $CH_2CH_2OCH_2CH_2$, $CH_2CH_2NR^5CH_2CH_2$ or $(CH_2)_{3-6}$,
wherein $R^5$ represents H; saturated or unsaturated, branched or unbranched, singly or multiply substituted or unsubstituted $C_{1-8}$-alkyl.

16. A substituted 4-aminocyclohexanol compound according to claim 1, wherein
$R^3$ represents unsubstituted or singly or multiply substituted phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl.

17. A substituted 4-aminocyclohexanol compound according to claim 4, wherein
$R^3$ represents unsubstituted or singly or multiply substituted thiophenyl, benzothiophenyl, pyridyl, furyl, benzofuranyl, benzodioxolanyl, indolyl, indanyl, benzodioxanyl, pyrrolyl, pyrimidyl or pyrazinyl.

18. A substituted 4-aminocyclohexanol compound according to claim 7, wherein
$R^3$ represents unsubstituted or singly or multiply substituted thiophenyl, benzothiophenyl, pyridyl, furyl, benzofuranyl, benzodioxolanyl, indolyl, indanyl, benzodioxanyl, pyrrolyl, pyrimidyl or pyrazinyl.

19. A substituted 4-aminocyclohexanol compound according to claim 5, wherein $R^3$ represents phenyl, naphthyl or anthracenyl.

20. A substituted 4-aminocyclohexanol compound according to claim 6, wherein $R^3$ represents phenyl, naphthyl or anthracenyl.

21. A substituted 4-aminocyclohexanol compound according to claim 1, wherein
$R^4$ represents unsubstituted or singly or multiply substituted $C_{3-8}$-cycloalkyl, aryl or heteroaryl; or —$R^8$-L-$R^9$.

22. A substituted 4-aminocyclohexanol compound according to claim 21, wherein
$R^8$ represents unsubstituted or singly or multiply substituted indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl;
L represents —C(O)—NH—, —NH—C(O)—, —C(O)—O—, —O—C(O)—, —O—, —S— or —S(O)$_2$—;
or $R^9$ represents unsubstituted or singly or multiply substituted indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl.

23. A substituted 4-aminocyclohexanol compound according to claim 1, wherein
$R^4$ represents —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$.

24. A substituted 4-aminocyclohexanol compound according to claim 23, wherein
$R^6$ represents H; saturated or unsaturated, branched or unbranched, singly or multiply substituted or unsubstituted $C_{1-4}$-alkyl; or saturated or unsaturated, branched or unbranched, singly or multiply substituted or unsubstituted $C(O)O$—$C_{1-4}$-alkyl.

25. A substituted 4-aminocyclohexanol compound according to claim 23, wherein
$R^7$ represents unsubstituted or singly or multiply substituted $C_{3-8}$-cycloalkyl, aryl or heteroaryl.

26. A substituted 4-aminocyclohexanol compound according to claim 8, wherein
$R^4$ represents unsubstituted or singly or multiply substituted heteroaryl; or —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH^2$—$CH_2R^7$ or —$C(Y)$—$CH_2$—$CH_2$—$CH_2R^7$; or —$R^8$-L-$R^9$
where $Y=H_2$.

27. A substituted 4-aminocyclohexanol compound according to claim 26, wherein
$R^6$ represents H, saturated or unsaturated, branched or unbranched, singly or multiply substituted or unsubstituted $C_{1-4}$-alkyl; or
$R^7$ represents unsubstituted or singly or multiply substituted indolyl, benzofuranyl, benzothiophenyl, indanyl, benzodioxanyl, benzodioxolanyl, acenaphthyl, carbazolyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl.

28. A substituted 4-aminocyclohexanol compound according to claim 26, wherein
$R^8$ represents unsubstituted or singly or multiply substituted indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl;
or $R^9$ represents unsubstituted or singly or multiply substituted indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl.

29. A substituted 4-aminocyclohexanol compound according to claim 9, wherein
$R^4$ represents —$CHR^6R^7$, —$CHR^6$—$CH_2R^7$ or —$CHR^6$—$CH_2$—$CH_2R^7$.

30. A substituted 4-aminocyclohexanol compound according to claim 29, wherein
  $R^6$ represents saturated or unsaturated, branched or unbranched, singly or multiply substituted or unsubstituted $C(O)O$—$C_{1-4}$-alkyl. or
  $R^7$ represents unsubstituted or singly or multiply substituted $C_{3-8}$-cycloalkyl, aryl or heteroaryl.

31. A substituted 4-aminocyclohexanol compound according to claim 10, wherein
  $R^4$ represents —$C(Y)R^7$, —$C(Y)$—$CH_2R^7$, —$C(Y)$ $CH^2$—$CH_2R^7$ or —$C(Y)$—$CH_2$—$CH_2$—$CH_2R^7$ where Y=O.

32. A substituted 4-aminocyclohexanol compound according to claim 31, wherein
  $R^7$ represents unsubstituted or singly or multiply substituted $C_{3-8}$-cycloalkyl, aryl or heteroaryl.

33. A substituted 4-aminocyclohexanol compound according to claim 1, wherein said compound is selected from the group consisting of:
  4-dimethylamino-1-(1-methyl-1H-indol-2-yl)-4-phenyl-cyclohexanol
  1-benzo[b]thiophen-2-yl-4-dimethylamino-4-phenylcyclohexanol
  1-benzo[b]thiophen-3-yl-4-dimethylamino-4-phenylcyclohexanol
  1-(1-benzenesulphonyl-1H-indol-2-yl)-4-dimethylamino-4-phenylcyclohexanol
  1-benzofuran-2-yl-4-dimethylamino-4-phenylcyclohexanol; and
  1-benzothiazol-2-yl-4-dimethylamino-4-phenylcyclohexanol, or
a salt thereof with a physiologically tolerated acid.

34. A pharmaceutical composition containing at least one substituted 4-aminocyclohexanol compound according to claim 1.

35. A pharmaceutical composition according to claim 34, wherein the pharmaceutical composition comprises an opioid or an anesthetic.

36. A method of alleviating pain or treating a locomotive disorder or administering an anticonvulsant or muscle relaxant, said method comprising the step of administering to a mammal in need thereof an effective amount of a compound according to claim 1.

37. A method of treating phobias, stress and syndromes associated with stress, depression, epilepsy, Alzheimer's disease, senile dementia, general cognitive dysfunction, learning difficulties and memory loss, withdrawal symptoms, alcohol abuse or dependency, drug abuse or dependency, sexual dysfunction, cardiovascular diseases, hypotension, hypertension, tinnitus, pruritus, defective hearing, defective bowel motility, impaired assimilation of food, anorexia, obesity, diarrhoea, cachexia, urinary incontinence or for providing an antitussive or anaesthetic or for co-administration during treatment with an opioid analgesic or with an anaesthetic, for diuresis, antinatriuresis or anxiolysis in a mammal, said method comprising administering to said mammal an effective amount of a substituted 4-aminocyclohexanol compound corresponding to formula I,

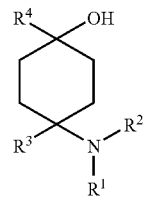

wherein
  $R^1$ and $R^2$ independently of one another represent H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl; wherein $R^1$ and $R^2$ are not both H, or the radicals $R^1$ and $R^2$ together form a ring and represent $CH_2CH_2OCH_2CH_2$, $CH_2CH_2NR^5CH_2CH_2$ or $(CH_2)_{3-6}$;
    wherein $R^5$ represents H; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted alkylene aryl bound via $C_{1-3}$, $C_{3-8}$-cycloalkyl or heteroaryl;
  $R^3$ represents unsubstituted or singly or multiply substituted aryl or heteroaryl;
  $R^4$ represents unsubstituted or singly or multiply substituted $C_{3-8}$-cycloalkyl, aryl or heteroaryl; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH^2$—$CH_2$—$CH_2R^7$; or —$R^8$-L-$R^9$
  wherein
  Y=O, S or $H_2$;
  $R^6$ represents H, saturated or unsaturated, branched or unbranched, singly or multiply substituted or unsubstituted $C_{1-7}$-alkyl; or saturated or unsaturated, branched or unbranched, singly or multiply substituted or unsubstituted $C(O)O$—$C_{1-6}$-alkyl;
  $R^7$ represents H; respectively unsubstituted or singly or multiply substituted $C_{3-8}$-cycloalkyl, aryl or heteroaryl;
  $R^8$ represents respectively unsubstituted or singly or multiply substituted aryl or heteroaryl;
  L represents —$C(O)$—NH—, —NH—$C(O)$—, —$C(O)$—O—, —O—$C(O)$—, —O—, —S— or —$S(O)_2$—; and
  $R^9$ represents unsubstituted or singly or multiply substituted aryl or heteroaryl,
or a salt thereof with a physiologically tolerated acid.

38. A method of producing a substituted 4-aminocyclohexanol compound corresponding to formula I of claim 1 comprising the steps of:
  a. reacting a cyclohexane-1,4-dione protected by the groups $S^1$ and $S^2$ according to formula II in the presence of a compound corresponding to formula $HNR^{01}R^{02}$ with a cyanide, to form a protected N-substituted 1-amino-4-oxo-cyclohexanecarbonitrile compound corresponding to formula III;

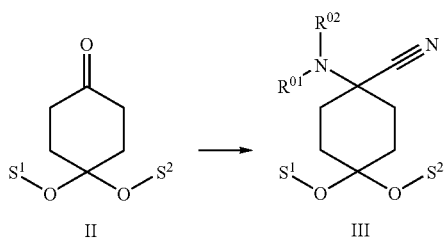

II → III b. reacting the compound corresponding to formula III with organometallic reagents corresponding to the formula metal-$R^3$ to form a compound corresponding to formula IVa;

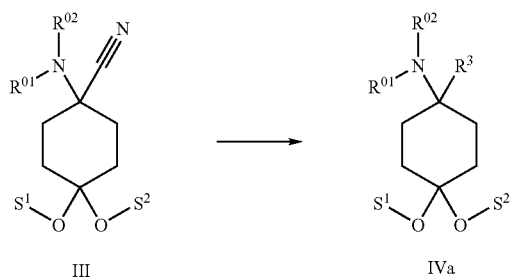

III → IVa c. removing the protective groups $S^1$ and $S^2$ on the compound corresponding to formula IVa to form a 4-substituted 4-aminocyclohexanone compound corresponding to formula IV;

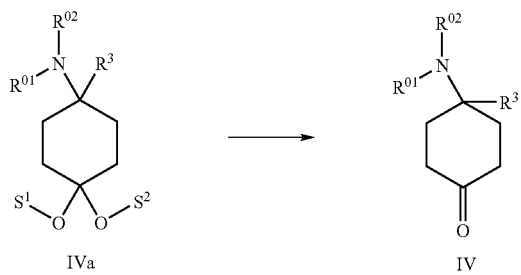

IVa → IV d. reacting the 4-substituted 4-aminocyclohexanone compound corresponding to formula IV with organometallic reagents corresponding to the formula metal-$R^{04}$ to form a compound corresponding to formula V;

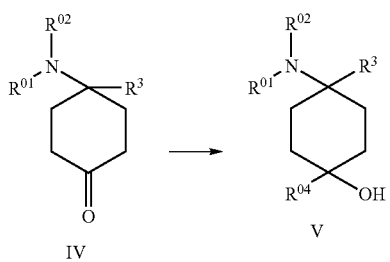

IV → V wherein
  $R^{01}$ and $R^{02}$ independently of one another represent H; H provided with a protective group; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl;
  or the radicals $R^{01}$ and $R^{02}$ together form a ring and represent $CH_2CH_2OCH_2CH_2$, $CH_2CH_2NR^{05}CH_2CH_2$ or $(CH_2)_{3-6}$,
    wherein $R^{05}$ represents H; H provided with a protective group; saturated or unsaturated, branched or unbranched, singly or multiply substituted or unsubstituted $C_{1-8}$-alkyl or $C_{3-8}$-cycloalkyl; singly or multiply substituted or unsubstituted aryl or heteroaryl; or singly or multiply substituted or unsubstituted aryl bound via $C_{1-3}$-alkylene, $C_{3-8}$-cycloalkyl or heteroaryl;
  $R^{04}$ represents H, H provided with a protective group; unsubstituted or singly or multiply substituted $C_{3-8}$-cycloalkyl, aryl or heteroaryl; —$CHR^{10}R^7$, —$CHR^{10}$—$CH_2R^7$, —$CHR^{10}$—$CH_2$—$CH_2R^7$, —$CHR^{10}$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$
    where $R^{10}$ represents H, saturated or unsaturated, branched or unbranched, singly or multiply substituted or unsubstituted $C_{1-7}$-alkyl; and
  $S^1$ and $S^2$ independently of one another represent protective groups or together represent a protective group.

39. The method of claim 38, wherein $S^1$ and $S^2$ together represent a monoacetal group.

40. The method of claim 38, wherein step a) further comprises:
  acylating, alkylating or sulfonating the compound corresponding to formula III in any sequence and optionally repeatedly; or
  where $R^{01}$, $R^{02}$ or $R^6$=H protected with a protective group, removing at least one protective group and optionally acylating, alkylating or sulfonating the compound corresponding to formula III; or
  where $R^1$ or $R^{02}$ or $R^6$=H, introducing at least one protective group and optionally acylating, alkylating or sulfonating the compound corresponding to formula III.

41. The method of claim 38, wherein step b) further comprises:
  acylating, alkylating or sulfonating the compound corresponding to formula IVa in any sequence and optionally repeatedly; or
  where $R^{01}$, $R^{02}$ or $R^6$=H protected with a protective group, removing at least one protective group and optionally acylating, alkylating or sulfonating the compound corresponding to formula IVa; or
  where $R^{01}$ or $R^{02}$ or $R^6$=H, introducing at least one protective group and optionally acylating, alkylating or sulfonating the compound corresponding to formula IVa.

42. The method of claim 38, wherein step c) further comprises:
  acylating, alkylating or sulfonating the compound corresponding to formula IV in any sequence and optionally repeatedly; or where $R^{01}$, $R^{02}$ or $R^6$=H protected with a protective group, removing at least one protective group and optionally acylating, alkylating or sulfonating the compound corresponding to formula IV; or where $R^{01}$ or $R^{02}$ or $R^6$=H, introducing at least one protective group and optionally acylating, alkylating or sulfonating the compound corresponding to formula IV.

43. The method of claim 38, wherein step d) further comprises:

acylating, alkylating or sulfonating the compound corresponding to formula V in any sequence and optionally repeatedly; or where $R^{01}$, $R^{02}$ or $R^6$=H protected with a protective group, removing at least one protective group and optionally acylating, alkylating or sulfonating the compound corresponding to formula V; or where $R^{01}$ or $R^{02}$ or $R^6$=H, introducing at least one protective group and optionally acylating, alkylating or sulfonating the compound corresponding to formula V.

44. The method of claim 38, wherein the protective groups on H in $R^{01}$, $R^{02}$, $R^{04}$ or $R^{05}$ are selected from the group consisting of alkyl groups, benzyl groups or carbamates.

45. The method of claim 44, wherein the protective groups on H in $R^{01}$, $R^{02}$, $R^{04}$ or $R^{05}$ are selected from the group consisting of fluorenylmethyl-chloroformate groups (FMOC), benzyloxycarbonyl (Z) and tert-butyloxycarbonyl (Boc).

46. The method of claim 38, wherein the cyanide of step a) is potassium cyanide.

47. The method of claim 38, wherein the organometallic reagents of step b) are Grignard or organolithium reagents.

48. The method of claim 38, wherein the organometallic reagents of step d) are Grignard or organolithium reagents.

49. The substituted 4-aminocyclohexanol compound corresponding to formula I of claim 1, wherein said compound is in the form of a salt with a physiologically tolerated acid.

50. The substituted 4-aminocyclohexanol compound corresponding to formula I of claim 1, wherein said compound is in the form of a hydrate.

51. The substituted 4-aminocyclohexanol compound corresponding to formula I of claim 1, wherein said compound is present in the form of a pure enantiomer or pure diastereoisomer.

52. The substituted 4-aminocyclohexanol compound corresponding to formula I of claim 1, wherein said compound is present in the form of a mixture of stereoisomers.

* * * * *